(12) United States Patent
Mayse et al.

(10) Patent No.: US 11,446,524 B2
(45) Date of Patent: Sep. 20, 2022

(54) SYSTEMS, DEVICES, AND METHODS FOR TREATING A PULMONARY DISEASE WITH ULTRASOUND ENERGY

(71) Applicant: Holaira, Inc., Plymouth, MN (US)

(72) Inventors: Martin L. Mayse, Wayzata, MN (US); Steven P. Mertens, Plymouth, MN (US); Steven C. Dimmer, Bellvue, WA (US)

(73) Assignee: Nuvaira Inc., Minneapolis, MN (US)

(*) Notice: Subject to any disclaimer, the term of this patent is extended or adjusted under 35 U.S.C. 154(b) by 257 days.

(21) Appl. No.: 15/021,555

(22) PCT Filed: Sep. 12, 2014

(86) PCT No.: PCT/US2014/055384
§ 371 (c)(1),
(2) Date: Mar. 11, 2016

(87) PCT Pub. No.: WO2015/038886
PCT Pub. Date: Mar. 19, 2015

(65) Prior Publication Data
US 2016/0220851 A1    Aug. 4, 2016

Related U.S. Application Data

(60) Provisional application No. 61/876,925, filed on Sep. 12, 2013.

(51) Int. Cl.
*A61B 18/00* (2006.01)
*A61N 7/02* (2006.01)
(Continued)

(52) U.S. Cl.
CPC ............... *A61N 7/02* (2013.01); *A61B 18/04* (2013.01); *A61B 18/1492* (2013.01);
(Continued)

(58) Field of Classification Search
CPC .. A61N 7/02; A61N 7/00; A61B 18/04; A61B 5/6853; A61M 25/0125;
(Continued)

(56) References Cited

U.S. PATENT DOCUMENTS 5,190,046 A * 3/1993 Shturman ................ A61B 8/12
600/459
8,088,127 B2    1/2012 Mayse et al.
(Continued)

FOREIGN PATENT DOCUMENTS

WO    WO 2011/060200 A1    5/2011

OTHER PUBLICATIONS

PCT/ISA/210 International Search Report for PCT/US2014/055384, dated Dec. 24, 2014, 4 pages.
(Continued)

*Primary Examiner* — Joanne M Hoffman
*Assistant Examiner* — Rachel A. Vierra
(74) *Attorney, Agent, or Firm* — Patterson Thuente Pedersen, P.A.

(57) ABSTRACT

A pulmonary treatment system includes a compact configuration for delivery to an airway of a patient. An energy delivery system of the pulmonary treatment system delivers ultrasound energy to target nerve tissue in or along an airway wall of the airway radially outward from surface tissue to reduce airway resistance in a downstream airway. The pulmonary treatment system may protect tissue in the airway wall of the airway located between the target nerve tissue and the ultrasound energy delivery system by a coolant system that may also act as a coupling fluid for the emitted ultrasound energy.

9 Claims, 23 Drawing Sheets

(51) Int. Cl.
*A61B 18/14* (2006.01)
*A61B 18/04* (2006.01)
A61M 25/10 (2013.01)
A61N 7/00 (2006.01)

(52) U.S. Cl.
CPC .... *A61N 7/022* (2013.01); *A61B 2018/00011* (2013.01); *A61B 2018/00023* (2013.01); *A61B 2018/00279* (2013.01); *A61B 2018/00285* (2013.01); *A61B 2018/00541* (2013.01); *A61B 2018/00577* (2013.01); *A61M 25/10* (2013.01); *A61N 2007/003* (2013.01); *A61N 2007/0078* (2013.01)

(58) Field of Classification Search
CPC .......... A61M 25/10; A61M 2025/1056; A61M 2025/1013; A61M 2025/1072
See application file for complete search history.

(56) References Cited

U.S. PATENT DOCUMENTS

| | | | |
|---|---|---|---|
| 8,911,439 | B2 | 12/2014 | Mayse et al. |
| 2004/0267132 | A1 | 12/2004 | Podany |
| 2006/0058711 | A1 | 3/2006 | Harhen et al. |
| 2006/0206137 | A1* | 9/2006 | Gazza ................. A61M 25/104 606/194 |
| 2008/0086073 | A1 | 4/2008 | McDaniel |
| 2009/0018446 | A1* | 1/2009 | Medan ................... A61N 7/022 600/439 |
| 2010/0179424 | A1 | 7/2010 | Warnking et al. |
| 2011/0112400 | A1* | 5/2011 | Emery ..................... A61B 8/12 600/439 |
| 2011/0152855 | A1* | 6/2011 | Mayse ............... A61B 18/1485 606/33 |
| 2011/0301587 | A1 | 12/2011 | Deem et al. |
| 2012/0209118 | A1 | 8/2012 | Warnking et al. |
| 2012/0232436 | A1 | 9/2012 | Warnking et al. |
| 2012/0310233 | A1 | 12/2012 | Dimmer et al. |
| 2013/0197555 | A1* | 8/2013 | Schaer ..................... A61N 7/00 606/170 |

OTHER PUBLICATIONS

PCT/ISA/237 Written Opinion for PCT/US2014/055384, dated Dec. 24, 2014, 23 pages.

* cited by examiner

SYSTEMS, DEVICES, AND METHODS FOR TREATING A PULMONARY DISEASE WITH ULTRASOUND ENERGY

RELATED APPLICATIONS

The present application is a National Phase entry of PCI Application No. PCT/US2014/055384, filed September 2014, which claims the benefit of U.S. Provisional Application No. 61/876,925 filed Sep. 12, 2013, and entitled "Systems, Devices, and Methods for Treating Pulmonary Disease with Ultrasound Energy" said applications being herein incorporated in their entireties by reference.

TECHNICAL FIELD

The present disclosure generally relates to treatment of pulmonary diseases, and more particularly to systems, devices, and methods for treating a pulmonary disease with ultrasound energy.

BACKGROUND

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough, breathlessness, and wheeze. In COPD, for example, breathlessness may be noticed when performing somewhat strenuous activities, such as running, jogging, brisk walking, etc. As the disease progresses, breathlessness may be noticed when performing non-strenuous activities, such as walking Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs, resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

A variety of solutions have been proposed for addressing pulmonary disorders, including COPD. One conventional treatment for COPD includes delivering the pharmaceutical drug tiotropium to the lungs via an inhaler. Typically, a patient places tiotropium capsules in a specially designed inhaler, and then breathes in dry powder contained in the capsules through the inhaler. This treatment must be administered on a recurring, sometimes daily, basis and its efficacy can be highly dependent on patient compliance.

Another conventional treatment includes maneuvering a catheter with an electrode to an affected area of the lungs and delivering thermal radiofrequency energy directly to the airway wall to directly heat the tissue and thereby reduce airway smooth muscle mass. This treatment, known as bronchial thermoplasty, requires patients to be treated over multiple sessions with each session targeting a different area of the lungs. Possible side-effects over the course of the treatments include asthma attacks, wheezing, chest discomfort, chest pain, partial collapse of the lungs, lower airway bleeding, anxiety, headaches, and nausea.

Several particularly effective treatments for pulmonary disorders are described in, for example, U.S. Pat. No. 8,088,127, titled, "Systems, Assemblies, and Methods for Treating a Bronchial Tree," and U.S. Patent Application Publication No. 2011/0152855, titled, "Delivery Devices with Coolable Energy Emitting Assemblies." In one example treatment described in these documents, a pulmonary treatment system delivers energy to damage a nerve trunk extending along a first airway of a patient, which thereby reduces airway resistance in a second airway distal to the first airway. This treatment provides numerous advantages over other, conventionally available treatments, including being far less invasive and requiring far fewer treatments.

BRIEF SUMMARY

It has been recognized that delivering ultrasound energy to an airway wall of a patient at a treatment location can affect nerves extending along the airway, thereby reducing airway obstruction in airways distal to the treatment location.

In one aspect, a pulmonary treatment system includes an elongate body and an ultrasound energy delivery assembly coupled to a distal end of the elongate body and being positionable into an airway of a patient. The ultrasound energy delivery assembly includes a deployable member having a seating portion which is movable from a delivery configuration into a deployed configuration in which the seating portion preferentially seats between adjacent cartilage rings in the airway, and an ultrasound energy emitter in a predetermined position relative to the seating portion in the deployed configuration and configured to deliver ablative ultrasound energy to nerve tissue spaced radially outward from surface tissue of the airway wall.

The ultrasound energy emitter may be configured to generate focused ultrasound energy. A focal length of the ultrasound energy emitter may be selected to target nerve tissue spaced radially outward from surface tissue of the airway wall. The ultrasound energy emitter may include an acoustic lens or a transducer with a curvilinear surface profile to focus the ultrasound energy.

The ultrasound energy emitter may be rotatable about a longitudinal axis.

The ultrasound energy emitter may include a plurality of ultrasound transducers circumferentially spaced about a longitudinal axis to generate a plurality of respective beams of ultrasound energy.

The deployable member comprises an expandable member to move the ultrasound energy delivery assembly from the delivery configuration to the deployed configuration. The pulmonary treatment system may further include a coupling fluid source in fluid communication with the expandable member to deliver a coupling fluid into the expandable member so as to provide acoustic coupling between the ultrasound energy emitter and the expandable member.

The pulmonary treatment system may further include a first acoustic barrier along a first side of the deployable member to assist in directing ultrasound energy radially outward from the deployable member. The pulmonary treatment system may further include a second acoustic barrier along a second side of the deployable member to assist in directing ultrasound energy radially outward from the deployable member. The first and second acoustic barriers may comprise expandable members.

The deployable member may include a curvilinear profile in the deployed configuration that is shaped to funnel ultrasound energy toward an area defined by an interface of the seating portion and the airway wall between the adjacent cartilage rings of the airway. The deployable member may have a curvilinear profile in the deployed configuration that is shaped to reflect a substantial portion of the ultrasound energy emitted by the ultrasound energy emitter toward an opposing side of the deployable member.

The ultrasound energy delivery assembly may further include an acoustic barrier coupled to the deployable member to reduce or eliminate the transmission of ultrasound energy through surface tissue of the airway wall adjacent the acoustic barrier.

In another aspect, a pulmonary treatment system includes an elongate body and an ultrasound energy delivery assembly coupled to a distal end of the elongate body and being positionable into an airway of a patient, the ultrasound energy delivery assembly including at least two ultrasound delivery elements respectively positioned to deliver energy through two different intercartilaginous spaces of the airway without repositioning the ultrasound energy delivery assembly.

Each of the ultrasound delivery elements of the ultrasound energy delivery assembly may be configured to generate focused ultrasound energy.

One of the ultrasound delivery elements may be configured to generate a first beam of ultrasound energy that overlaps with a second beam of ultrasound energy generated by another one of the ultrasound delivery elements. The first beam and the second beam may overlap within an area radially outward from a cartilage ring.

The ultrasound energy emitter may include at least one seating element configured to locate at least one ultrasound delivery element in an intercartilaginous space between adjacent cartilage rings of the airway.

In another aspect, a pulmonary treatment system includes an elongate body and an ultrasound energy delivery assembly coupled to a distal end of the elongate body and being positionable into an airway of a patient, the ultrasound energy delivery assembly including two ultrasound delivery elements and at least one seating element configured to locate the two ultrasound delivery elements on opposite sides of a cartilage ring of the airway.

Each of the ultrasound delivery elements of the ultrasound energy delivery assembly may be configured to generate focused ultrasound energy.

A first one of the ultrasound delivery elements may be configured to generate a first beam of ultrasound energy that overlaps with a second beam of ultrasound energy generated by a second one of the ultrasound delivery elements. The first beam and the second beam may overlap within an area radially beyond a cartilage ring.

In another aspect, a pulmonary treatment system includes an elongate body and an ultrasound energy delivery assembly coupled to a distal end of the elongate body and being positionable into an airway of a patient, the ultrasound energy delivery assembly including a plurality of ultrasound energy delivery elements and at least one positioning element configured to locate the plurality of ultrasound energy delivery elements relative to cartilage rings in the airway such that a cartilage ring is positioned between at least one pair of the ultrasound energy delivery elements.

Each of the ultrasound delivery elements of the ultrasound energy delivery assembly may be configured to generate focused ultrasound energy.

One of the ultrasound delivery elements may be configured to generate a first beam of ultrasound energy that overlaps with a second beam of ultrasound energy generated by another one of the ultrasound delivery elements. The first beam and the second beam may overlap within an area radially beyond a cartilage ring.

In another aspect, a pulmonary treatment system includes an elongate body and an ultrasound energy delivery assembly coupled to a distal end of the elongate body and being positionable into an airway of a patient. The ultrasound energy delivery assembly may include an apposition member, a fluid conduit that extends along a lateral side of the apposition member, and an ultrasound energy emitter disposed along the fluid conduit and configured to deliver ultrasound energy to target nerve tissue spaced radially outward from surface tissue of the airway wall, the apposition member configured to bring the fluid conduit in contact with an airway wall of a patient during delivery of ultrasound energy to the target nerve tissue.

The apposition member may be an inflatable member in fluid communication with a fluid supply source.

The ultrasound energy emitter may include at least one ultrasound delivery element positioned within the fluid conduit.

The fluid conduit may extend longitudinally along the lateral side of the apposition member and the at least one ultrasound delivery element extend parallel to the fluid conduit.

The pulmonary treatment system may further include an optical system configured to provide a viewable image of the ultrasound energy emitter during delivery of ultrasound energy. The apposition member may be configured to be optically coupled to a lens of an optical system positioned in the airway proximally or distally of the apposition member such that the ultrasound energy emitter is viewable during delivery of ultrasound energy.

In another aspect, a pulmonary treatment system includes an elongate body and an ultrasound energy delivery assembly coupled to a distal end of the elongate body and being positionable into an airway of a patient. The ultrasound energy delivery assembly may include a deployable member that is movable from a collapsed, delivery state to an expanded, deployed state, and an ultrasound energy emitter configured to delivery ultrasound energy to target nerve tissue spaced radially outward from surface tissue of the airway wall. The ultrasound energy emitter may be positioned within the deployable member, and the ultrasound energy emitter may be movable relative to the deployable member when the deployable member is in the deployed state to adjust a distance between an ultrasound energy delivery element thereof and the surface tissue of the airway wall.

The deployable member may an expandable member. The expandable member may be in fluid communication with a supply lumen and a return lumen to enable an acoustic coupling fluid to circulate through the expandable member.

The ultrasound energy emitter may be rotatable around the central longitudinal axis.

The pulmonary treatment system may further include an optical system configured to provide a viewable image of the ultrasound energy emitter during delivery of ultrasound energy. The deployable member may be configured to be optically coupled to a lens of an optical system positioned in the airway proximally or distally of the deployable member such that the ultrasound energy emitter is viewable during delivery of ultrasound energy.

In another aspect, a pulmonary treatment system includes an elongate body and an ultrasound energy delivery assembly coupled to a distal end of the elongate body and being positionable into an airway of a patient. The ultrasound energy delivery assembly may include an acoustic coupling member, an ultrasound energy emitter acoustically coupled to the acoustic coupling member and configured to deliver ultrasound energy to target nerve tissue spaced radially outward from surface tissue of the airway wall, and a biasing element arranged to urge the acoustic coupling member away from a non-treatment side of the airway wall into contact with an opposing side of the airway wall.

The biasing element may comprise an expandable member. The acoustic coupling member may comprise an expandable element. The expandable element and the expandable member may each be in fluid communication with a respective supply lumen to enable independent expansion thereof.

The acoustic coupling member may be in fluid communication with a supply lumen and a return lumen to enable an acoustic coupling fluid to circulate through the acoustic coupling member.

The pulmonary treatment system may further include an optical system configured to provide a viewable image of the ultrasound energy emitter during delivery of ultrasound energy. The acoustic coupling member may be configured to be optically coupled to a lens of an optical system positioned in the airway proximally or distally of the acoustic coupling member such that the ultrasound energy emitter is viewable during delivery of ultrasound energy.

In another aspect, a pulmonary treatment system may include an elongate body and an ultrasound energy delivery assembly coupled to a distal end of the elongate body and being positionable into an airway of a patient, the airway having first and second interior surfaces on opposing sides thereof. The ultrasound energy delivery assembly may have an ultrasound delivery element movable from a delivery state to a deployed state, wherein, in the deployed state, the ultrasound delivery element is closer to the first interior surface than the second interior surface.

The ultrasound energy delivery assembly may include a biasing element arranged to urge the ultrasound delivery element away from a non-treatment side of the airway wall.

The pulmonary treatment system may further comprise an expandable member for moving the ultrasound delivery element from the delivery state to the deployed state. The expandable member may be in fluid communication with a supply lumen and a return lumen to enable an acoustic coupling fluid to circulate through the expandable member.

In another aspect, a pulmonary treatment system includes an elongate body and an ultrasound energy delivery assembly coupled to a distal end of the elongate body and being positionable into an airway of a patient. The ultrasound energy delivery assembly is movable from a collapsed configuration having a collapsed cross-section to an expanded configuration having an expanded cross-section, the collapsed cross-section having a collapsed transverse dimension not more than about 6 mm and the expanded cross-section having an expanded transverse dimension of at least about 7 mm so as to contact an airway wall of the patient. The ultrasound energy delivery assembly includes an ultrasound energy emitter configured to delivery ultrasound energy through surface tissue of the airway wall to target tissue spaced radially outward from the surface tissue. The ultrasound energy emitter comprises a piezoelectric ultrasound delivery element that includes an energy emitting portion that is at least about 7 mm in length. The ultrasound energy delivery assembly further includes a cooling member configured to cool the surface tissue while the ultrasound energy emitter delivers ultrasound energy to the target tissue.

The ultrasound energy emitter may be configured to radiate ultrasound energy in a plurality of directions about a longitudinal axis of the ultrasound energy emitter.

The ultrasound energy emitter may include an acoustic lens to focus the emitted ultrasound energy. The acoustic lens may include a lens chamber in fluid communication with a supply lumen.

The cooling member may be in fluid communication with a coolant supply lumen and a coolant return lumen such that coolant may be continuously circulated through the cooling member during ultrasound energy delivery to target tissue in the airway wall. The cooling member may be configured to cool airway wall tissue located radially between the ultrasound energy emitter and the target tissue to protect the airway wall tissue from permanent damage when the ultrasound energy emitter delivers ultrasound energy to the target tissue. The cooling member may be configured to be filled with a coolant, the coolant remaining static in the cooling member during ultrasound energy delivery.

In another aspect, a method of treating a subject includes positioning an ultrasound energy delivery assembly having an ultrasound emitter and a deployable member with a seating portion within an airway such that the seating portion is aligned between adjacent cartilage rings, acoustically coupling the ultrasound emitter with an airway wall, and delivering ultrasound energy from the ultrasound energy delivery assembly to the airway wall to damage nerve tissue of a nerve trunk spaced radially outward from surface tissue of the airway wall such that nervous system signals transmitted to a portion of the bronchial tree are attenuated.

The deployable member may be an expandable member, and acoustically coupling the ultrasound emitter with the airway wall may comprise inflating the expandable member between the ultrasound emitter and the airway wall.

The method may further comprise cooling the surface tissue by circulating a cooled fluid through the expandable member.

The seating portion of the deployable member may be expandable to a diameter about equal to an inner diameter of the cartilage rings or to a diameter larger than an inner diameter of the cartilage rings.

Delivering ultrasound energy from the ultrasound energy delivery assembly to the airway wall may include focusing the ultrasound energy in a zone that is located between the adjacent cartilage rings and spaced radially outward from surface tissue of the airway wall.

The method of treating the subject may further include directing coolant toward an interface between the ultrasound energy delivery assembly and the airway wall where the ultrasound energy passes during a treatment procedure.

In another aspect, a method of treating a subject includes positioning an ultrasound energy delivery assembly within an airway such that a cartilage ring of the airway is between a pair of ultrasound energy delivery elements of the ultrasound energy delivery assembly, and delivering ultrasound energy from the ultrasound energy delivery elements to the airway wall to damage nerve tissue of a nerve trunk such that nervous system signals transmitted to a portion of the bronchial tree are attenuated. Delivering ultrasound energy from the ultrasound energy delivery elements to the airway wall may include focusing ultrasound energy from each of the ultrasound energy delivery elements within a common zone located radially outward from the cartilage ring. The method may further include directing coolant toward an interface between the ultrasound energy delivery assembly and the airway wall where the ultrasound energy passes during a treatment procedure.

In another aspect, a method of treating a subject includes positioning an ultrasound energy delivery assembly in an airway of the subject, apposing the ultrasound energy delivery assembly against an inner surface of an airway wall with an ultrasound transducer thereof positioned within an acoustic fluid chamber that is adjacent or within an expandable member of the ultrasound energy delivery assembly, and delivering ultrasound energy from the ultrasound transducer to nerve tissue spaced radially outward from the surface tissue of the airway wall. The method may further include circulating fluid within the acoustic fluid chamber to actively cool an interface between the ultrasound energy delivery assembly and the airway wall where the ultrasound energy passes during a treatment procedure.

In another aspect, a method of treating a subject includes positioning an ultrasound energy delivery assembly within an airway of the subject, the ultrasound energy delivery assembly having an ultrasound transducer, adjusting a radial position of the ultrasound transducer within an expandable acoustic fluid chamber surrounding the ultrasound transducer, and delivering ultrasound energy from the ultrasound transducer to the airway wall to damage nerve tissue of a nerve trunk such that nervous system signals transmitted to a portion of the bronchial tree are attenuated. The method may further include circulating fluid within the acoustic fluid chamber to actively cool an interface between the ultrasound energy delivery assembly and the airway wall where the ultrasound energy passes during a treatment procedure.

In another aspect, a method of treating a subject includes positioning an ultrasound energy delivery assembly within an airway of the subject, biasing an ultrasound transducer of the ultrasound energy delivery assembly away from a non-treatment side of the airway wall such that the ultrasound transducer is acoustically coupled with a treatment side of the airway wall, and delivering ultrasound energy from the ultrasound transducer to the treatment side of the airway wall to damage nerve tissue of a nerve trunk such that nervous system signals transmitted to a portion of the bronchial tree are attenuated. The ultrasound transducer may be acoustically coupled to the treatment side of the airway wall by a fluid within an acoustic fluid chamber surrounding the ultrasound transducer. The method may further include circulating fluid within the acoustic fluid chamber to actively cool an interface between the ultrasound energy delivery assembly and the airway wall where the ultrasound energy passes during a treatment procedure.

BRIEF DESCRIPTION OF THE DRAWINGS

The drawings discussed in the detailed description are described briefly as follows, in which.

DETAILED DESCRIPTION

Figure 7:
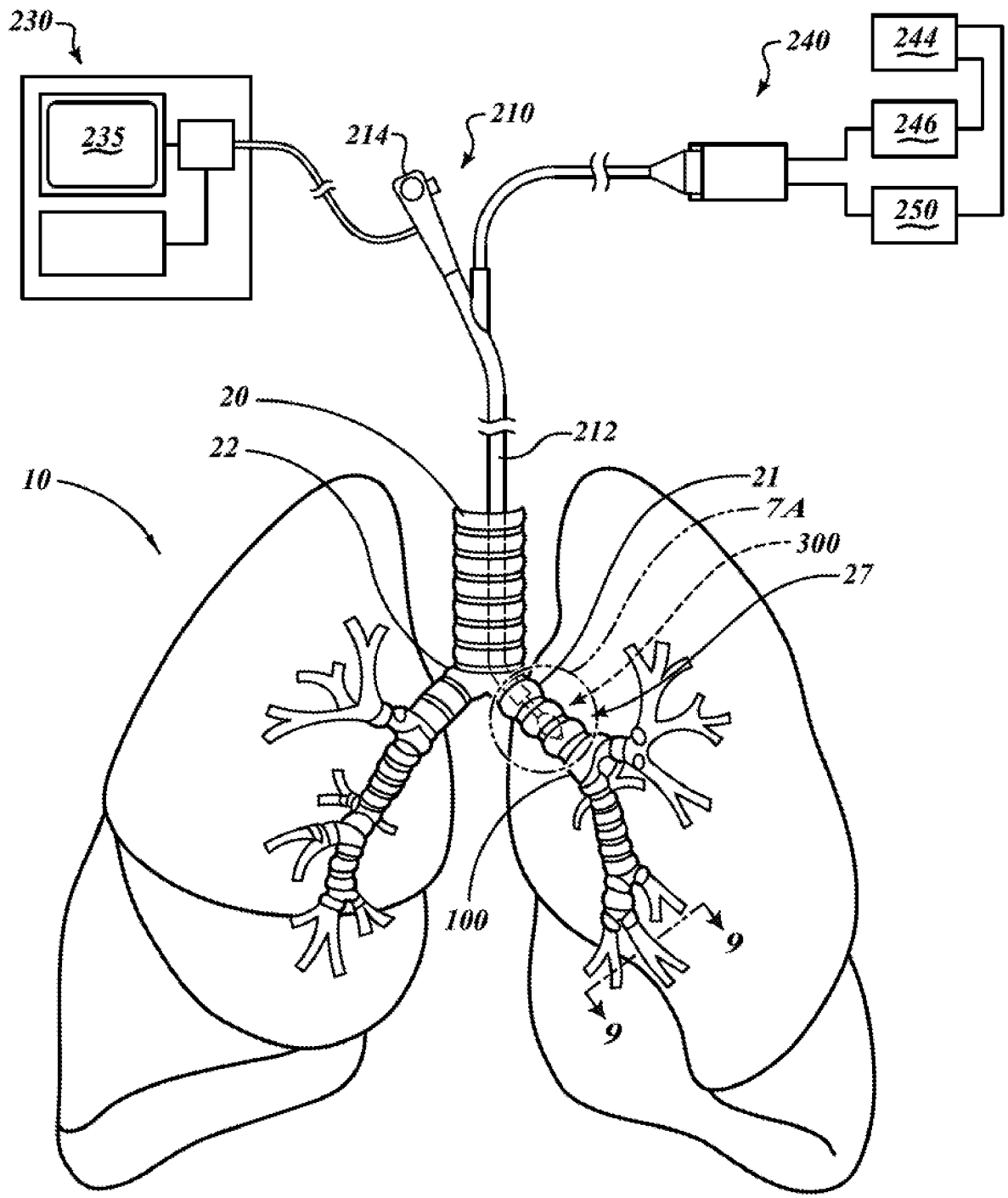
FIG. 7 is a schematic illustration of a pulmonary treatment system during a treatment session according to one aspect.
Figure 8:
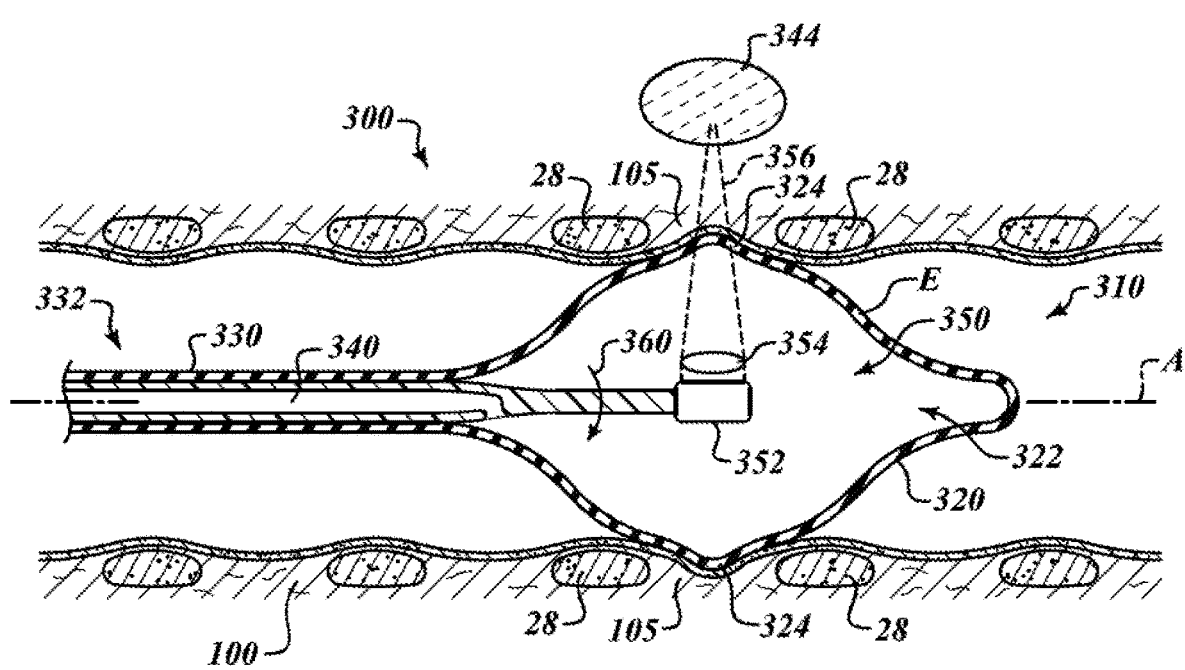
FIG. 8 is a cross-sectional view of the pulmonary treatment system of FIG. 7 positioned within an airway during treatment.
Figure 9:
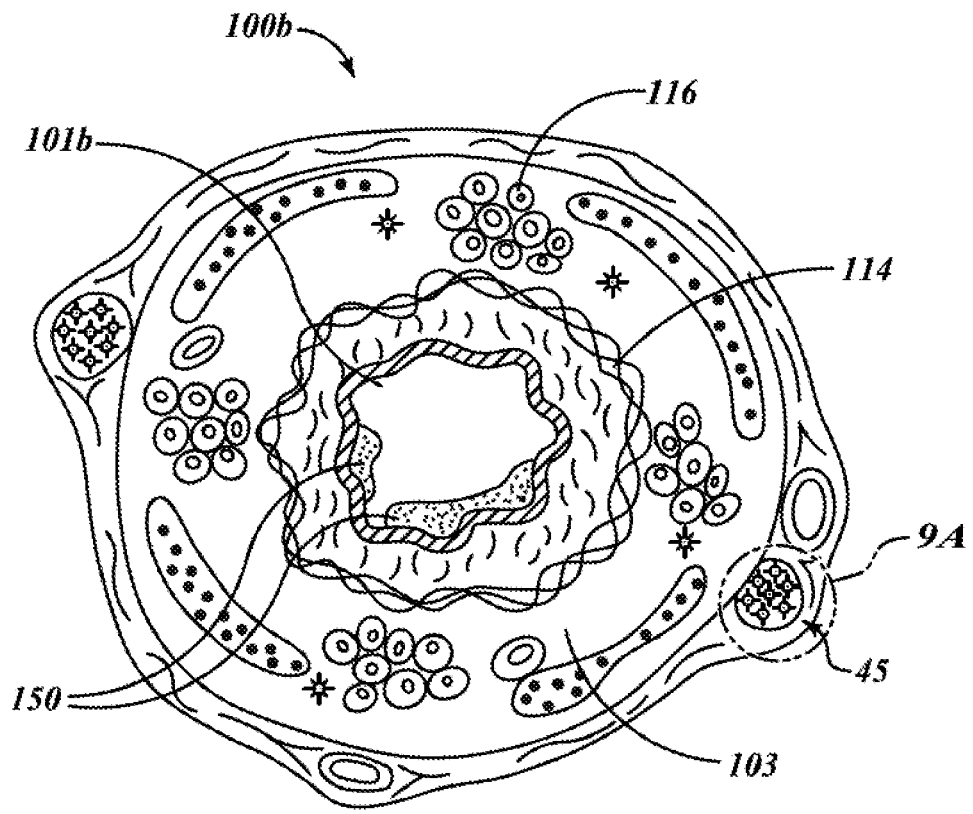
FIG. 9 is a cross-sectional view of a distal airway in the lung prior to treatment, taken along line 9-9 of FIG. 7.
Figure 10:
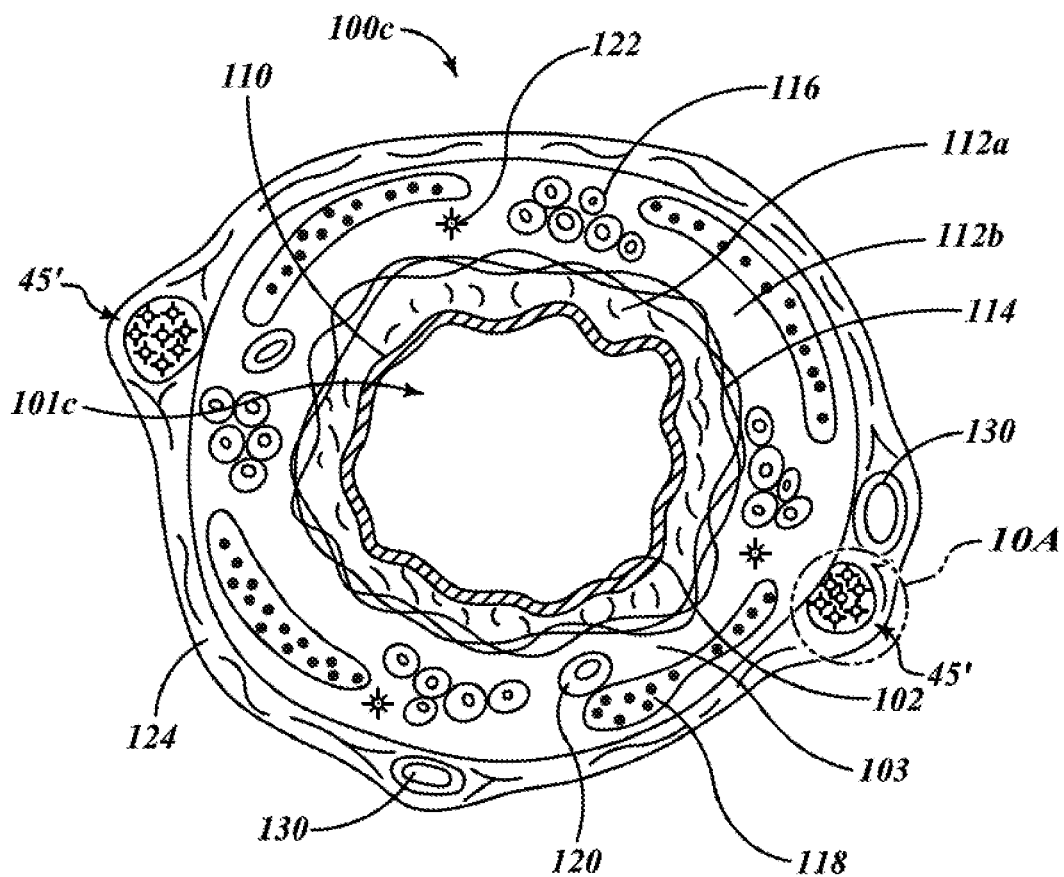
FIG. 10 is a cross-sectional view of the distal airway of FIG. 9 after a treatment.

FIGS. 1-6 provide an overview of human lung function and the role the nervous system can play in a diseased lung. FIGS. 7-8 provide an overview of an example treatment applied to the pulmonary system according to one aspect of the present disclosure. FIGS. 9-10 provide an overview of the effects of the treatment illustrated in FIGS. 7-8. FIGS. 11-34 illustrate further example aspects of the present disclosure.

Figure 1:
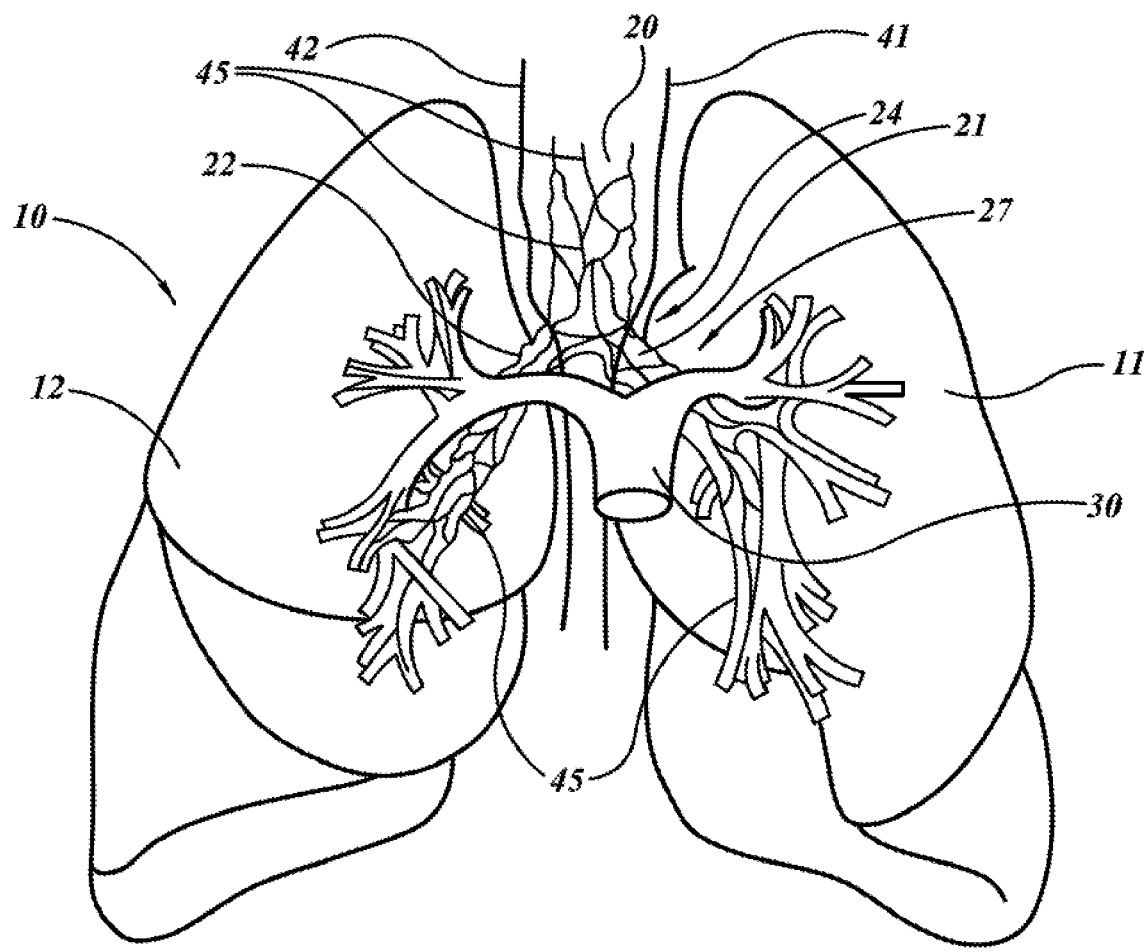
FIG. 1 is an anterior view of the lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and a right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The primary function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen-enriched blood then flows from the alveolar capillaries through the branching blood vessels of the pulmonary venous system to the heart. The heart pumps the oxygen-rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

The nervous system provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

Some of the nerve tissue in the network of nerve trunks 45 coalesce into other nerves (e.g., nerves connected to the esophagus, nerves though the chest and into the abdomen, and the like). Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways, as discussed in connection with FIGS. 3 and 4.

Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond to irritants, and stretch to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion.

Figure 2:
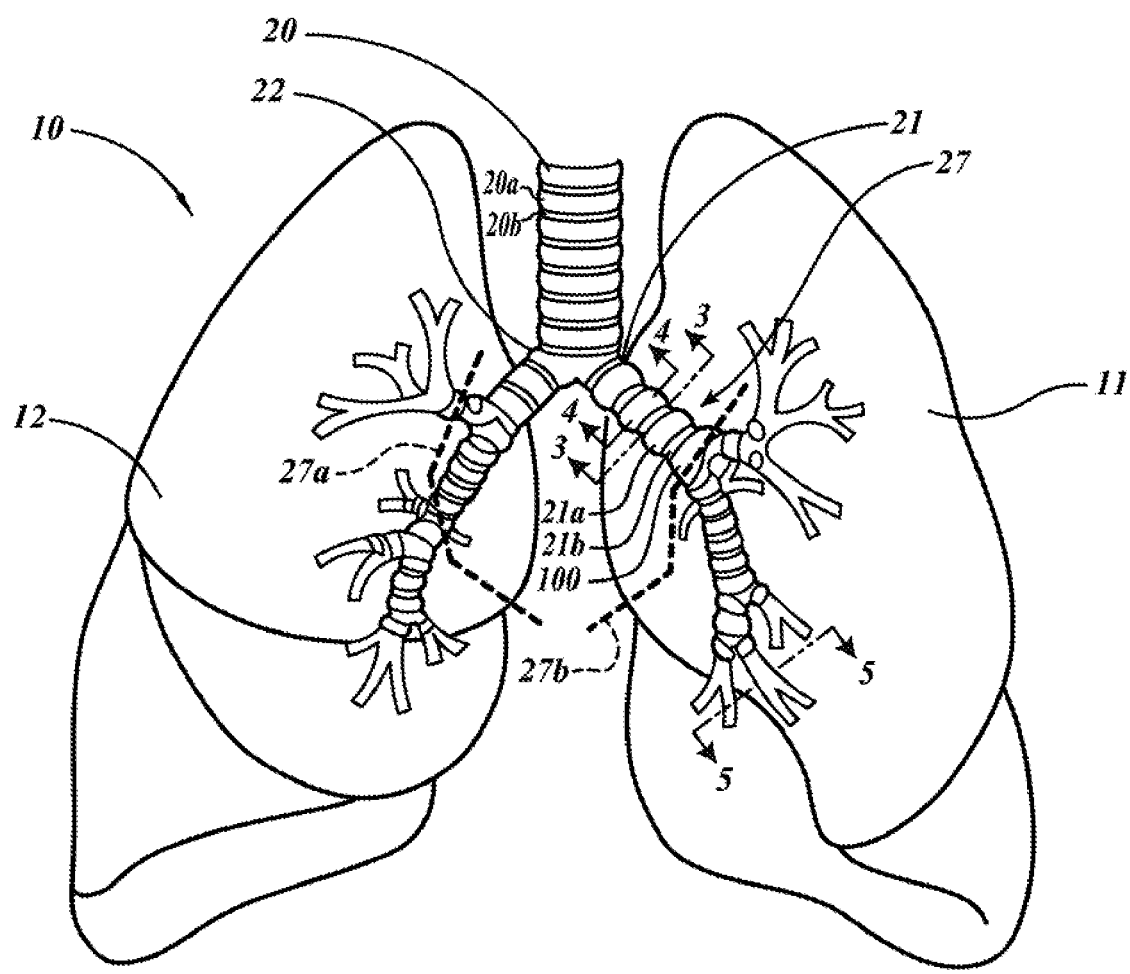
FIG. 2 is a further anterior view of the lungs of FIG. 1.

FIG. 2 is an anterior view of the lungs 10, 11; the trachea 20; and the bronchial tree 27. FIG. 2 includes a generalized illustration of the structure imposed by cartilage rings on the trachea 20 and bronchial tree 27. Portion 20a of the trachea 20 in FIG. 2 represents a portion of the trachea 20 that includes a cartilage ring, and portion 20b represents a portion of the trachea 20 between adjacent cartilage rings. Likewise, portion 21a represents a portion of the left main bronchus 21 that includes a cartilage ring, and portion 21b represents a portion of the left main bronchus 21 between adjacent cartilage rings. For ease of representation, the number of cartilage rings has been reduced and the spacing between the cartilage rings has been increased.

Notably, cartilage rings in the trachea do not extend around the entire circumference of the trachea, but instead are discontinuous on a posterior side of the trachea, which faces the esophagus. The discontinuity of the cartilage rings accommodates expansion of the esophagus into the tracheal space, for example, as food is swallowed. The shape of cartilage rings contributes to the cross-sectional shape of the trachea. Studies of the trachea have revealed a diversity of cross-sectional shapes in different patients, including elliptical, C-shaped, U-shaped, D-shaped, triangular, and circular. In addition, the cross-sectional shape of the trachea can change during the respiratory cycle from, for example, an elliptical shape during inspiration to, for example, a horseshoe shape during exhalation.

Figure 3:
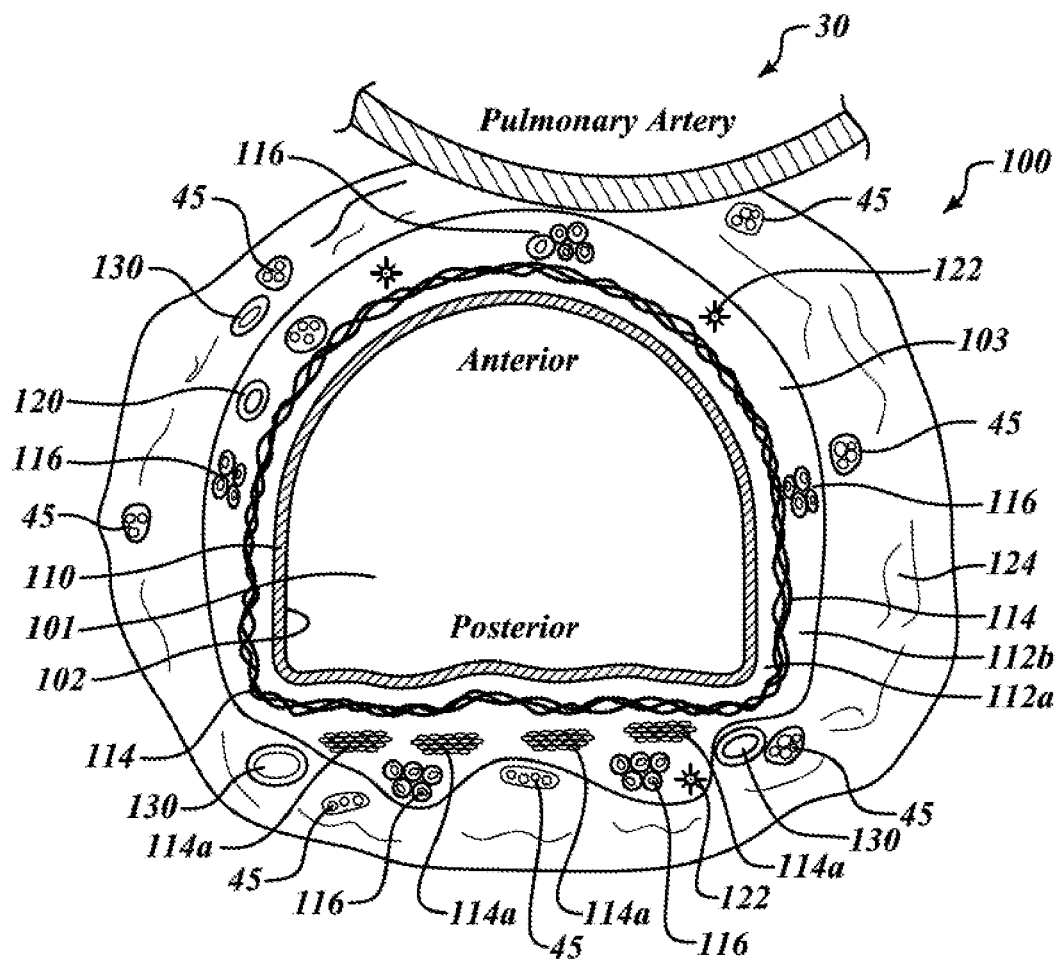
FIG. 3 is a cross-sectional view of a main stem bronchus between two adjacent cartilage rings, taken along line 3-3 of FIG. 2.
Figure 4:
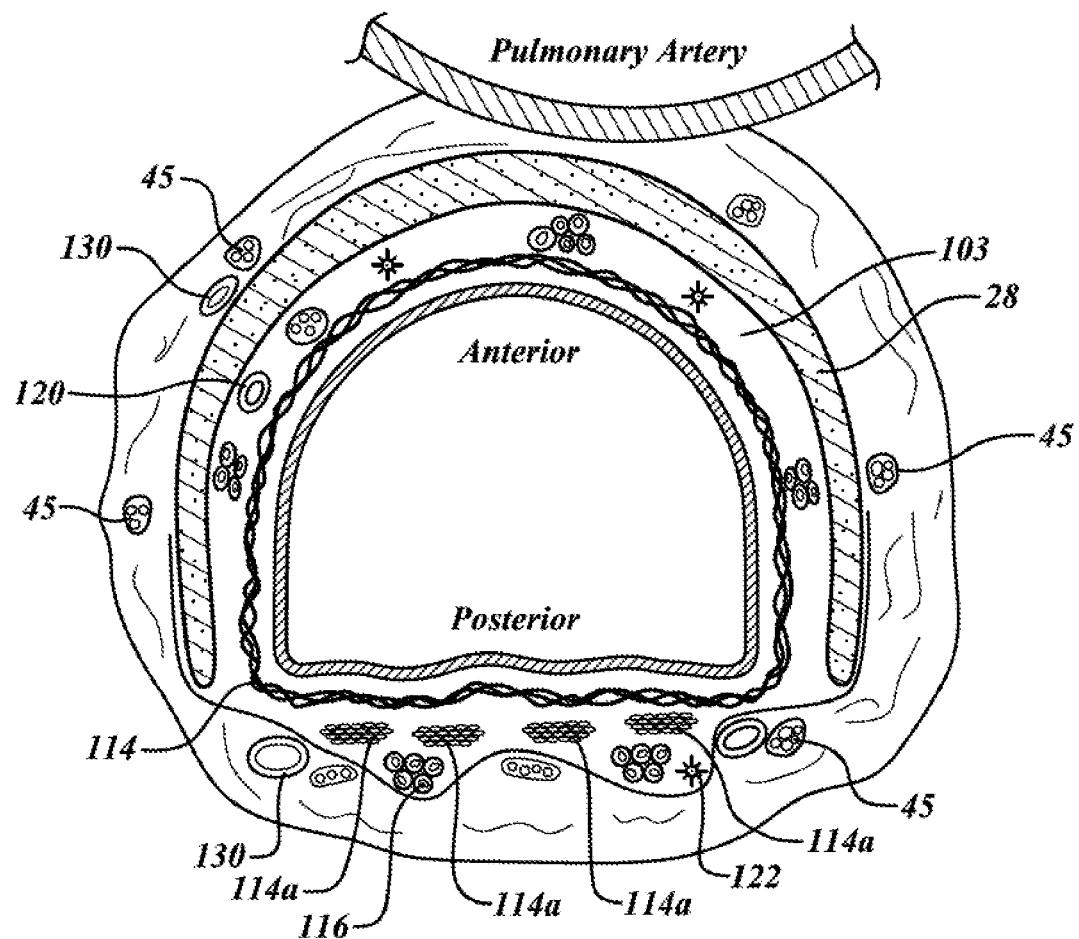
FIG. 4 is a cross-sectional view of a main stem bronchus through one of the cartilage rings, taken along line 4-4 of FIG. 2.

The cartilage rings in the left and right main bronchus are also incomplete. FIG. 3 is a cross-sectional view of a portion of an airway 100 in the left main bronchus 21 that is located between adjacent cartilage rings. FIG. 4 is a cross-sectional view of the airway 100 in portion of the left main bronchus 21 that includes a cartilage ring 28. In this example, the C-shaped cartilage ring 28 contributes to the D-shaped cross-sectional shape of the illustrated portion of the left main bronchus 21. The pulmonary artery 30 extends along an anterior side of the airway 100.

The airway 100 includes a lumen 101 defined by an inner surface 102 of the airway 100. The illustrated inner surface 102 is defined by a folded layer of epithelium 110 surrounded by stroma 112a. A layer of smooth muscle tissue 114 surrounds the stroma 112a. A layer of stroma 112b is between the muscle tissue 114 and connective tissue 124. Mucous glands 116, blood vessels 120, and nerve fibers 122 are within the stroma layer 112b. Smooth muscle bands 114a extend longitudinally along the posterior side of the airway 100, which is relatively loose when compared to the other portions of the airway 100 that are supported by the cartilage rings 28. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 and mucous glands 116 via the nerve fibers 122. Additionally, signals are transmitted from sensory receptors (e.g., cough, irritant, and stretch) through the nerve trunks 45 to the central nervous system.

Figure 5:
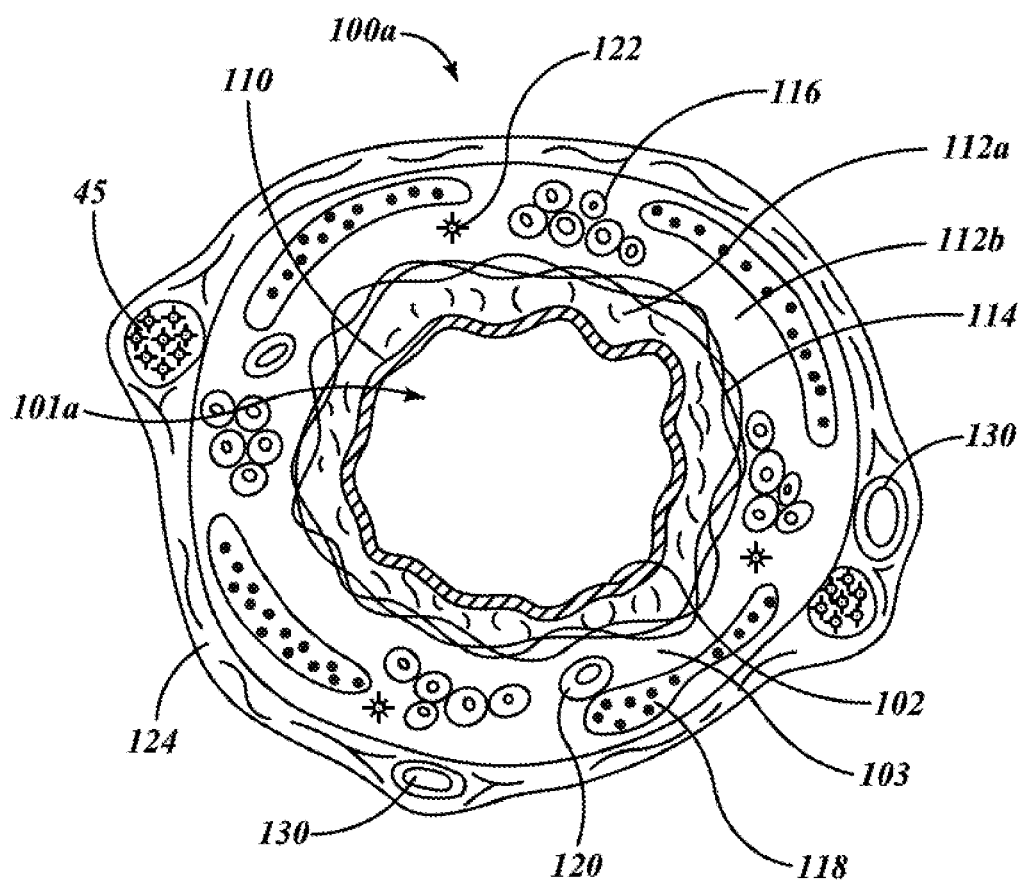
FIG. 5 is a cross-sectional view of a healthy distal airway in the lung, taken along line 5-5 of FIG. 2.
Figure 6:
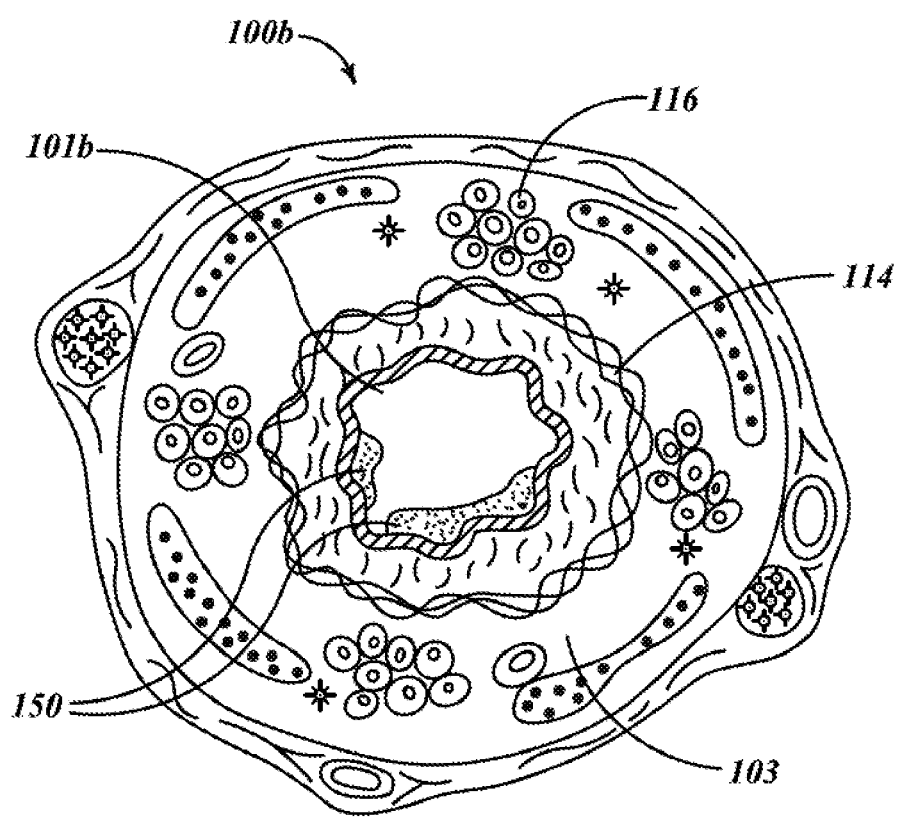
FIG. 6 is a cross-sectional view of the distal airway in FIG. 5 in which the airway is in an unhealthy constricted state, and mucus is in an airway lumen.

FIGS. 5 and 6 illustrate cross-sectional views of higher generation airways in healthy and diseased lungs, respectively. For the purpose of this disclosure, airway branches are numbered in generations starting down from the main stem at generation 0, continuing to the main bronchi at generation 1, and on to the more distal branches at generation 2 and higher. FIG. 5 is a cross-sectional view of a distal airway 100a of the bronchial tree 27 in a healthy lung. FIG. 6 is a cross-sectional view of a distal airway 100b that is affected by a pulmonary disease. The representation in FIGS. 5 and 6 is a generalized view that is intended to be representative of airways distal of the dashed lines 27a and 27b in FIG. 2. The example airways 100a and 100b include cartilage plates 118 rather than cartilage rings 28.

The lumen 101b of the airway 100b in FIG. 6 is significantly narrower than the lumen 101a of the healthy airway 100a, and is partially blocked by excess mucus 150. Depending on the patient, the reduced size of the lumen 101b can be attributable to variety of ailments, including, for example, inflammation of the airway wall 103, constriction of the smooth muscle tissue 114, or excessive intraluminal mucus or edema fluid, or both.

FIGS. 7 and 8 provide an overview of one example method and system that can be used to treat diseased airways such as the one shown in FIG. 6. It has been found that attenuating the transmission of signals traveling along the vagus nerves 41, 42 can alter airway smooth muscle tone, airway mucus production, airway inflammation, and the like in airways distal to the treatment site. Attenuation can include, without limitation, hindering, limiting, blocking, and/or interrupting the transmission of signals. For example, the attenuation can include decreasing signal amplitude of nerve signals or weakening the transmission of nerve signals.

Figure 7A:
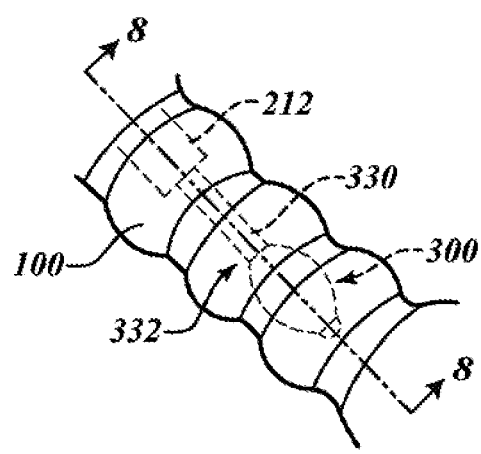
FIG. 7A is a schematic illustration of the pulmonary treatment system of FIG. 7 positioned within a left main bronchus according to one aspect.

FIGS. 7 and 7A illustrate a pulmonary treatment system 300 positioned within the left main bronchus 21 of a patient for a treatment session. In this example, the pulmonary treatment system 300 is advanced to the treatment site via a working channel of a flexible bronchoscope 210. Utilizing the working channel of a flexible bronchoscope to position a pulmonary treatment system in a patient's airway has numerous benefits, including obviating the need to separately navigate the bronchoscope and the pulmonary treatment system to the treatment site, providing a repeatable delivery location for the pulmonary treatment system, and improving visualization of the delivery and treatment.

Although the a pulmonary treatment systems described herein advantageously allow for a compact profile that facilitates compatibility with the working channel of a flexible bronchoscope, the aspects described herein are not so limited. For example, as will be readily apparent to one of ordinary skill in the art upon a complete review of the present disclosure, the aspects disclosed herein are also scalable to be compatible with larger working lumens that may or may not be associated with a bronchoscope. Notably, the present disclosure is not limited solely to systems that are delivered via the working channel of a bronchoscope, but also encompasses systems delivered by other means, such as an independent sheath and/or delivery catheter.

FIG. 7 further illustrates a delivery sheath 212 of the bronchoscope extending from a control section 214 external to the patient body, through the trachea 20, and to a treatment site within the left main bronchus 21. The bronchoscope 210 can be coupled to a video system 230, which allows a practitioner to observe progress of the delivery sheath 212 through the patient on a monitor 235 as the delivery sheath 212 is steered with the assistance of the control section 214. The video system 230 may be configured to display images generated in connection with an imaging system deployed with or integrated with the pulmonary treatment system 300. In some embodiments, the pulmonary treatment system 300 may be configured to circumferentially image a wall of the airway to localize the nerve trunks 45 and/or the bronchial arteries 130 prior to treatment using ultrasound energy.

Although the pulmonary treatment system 300 is positioned in the left main bronchi in this example, the pulmonary treatment system 300 can be positioned in other locations outside the lung, such as within the right main bronchi, the lobar bronchi, and bronchus intermedius. The bronchus intermedius is the portion of the right main bronchus between the upper lobar bronchus and the origin of the middle and lower lobar bronchi. The pulmonary treatment system 300 can also be positioned in higher generation airways (e.g., airway generations >2) to affect remote distal portions of the bronchial tree 27. The pulmonary treatment system 300 can be navigated through tortuous airways to perform a wide range of different procedures, such as, for example, to deliver ultrasound energy to affect nerve activity in a portion of a lobe, an entire lobe, multiple lobes, or one lung or both lungs. In some aspects, the lobar bronchi are treated to affect nerve activity in lung lobes. For example, one or more treatment sites along a lobar bronchus may be targeted to affect nerve activity in an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

In this example, the pulmonary treatment system 300 is coupled to a steering mechanism 240 and a fluid supply source 250 that is configured to supply fluid for acoustic coupling and/or cooling purposes. The pulmonary treatment system 300 is also coupled to an ultrasound energy excitation source 246 and a controller 244, which are configured to, in combination with the pulmonary treatment system 300, generate and deliver ultrasound energy to target airway tissue in a controlled manner. The controller 244 may include, without limitation, one or more processors, microprocessors, digital signal processors (DSPs), field programmable gate arrays (FPGA), and/or application-specific integrated circuits (ASICs), memory devices, buses, power sources, and the like. For example, the controller 244 can include a processor in communication with one or more memory devices. Buses can link an internal or external power supply to the processor. The memories may take a variety of forms, including, for example, one or more buffers, registers, random access memories (RAMs), and/or read only memories (ROMs). The controller 244 may also include various input and output devices, such as, for example, a display, a keyboard, touchpad, or the like and can be operated by a user to control the pulmonary treatment system 300. The controller 244 may be configured to control the fluid supply source 250 in coordination with the ultrasound energy excitation source 246 to appropriately balance the amount of ultrasound energy delivered to target tissue with the amount of energy which may be removed from surface tissue of the airway via interaction with cooling provided by the fluid supply source 250 to achieve various results described herein.

For example, the pulmonary treatment system 300 directs ultrasound energy to an airway wall at a treatment site to affect activity of the nerves 122 or the nerve trunks 45 at the treatment site. As noted above, it has been found that attenuating the transmission of nervous system signals can alter airway smooth muscle tone, airway mucus production, airway inflammation, and the like in airways distal to the treatment site. Attenuation can include, without limitation, hindering, limiting, blocking, and/or interrupting the transmission of signals. For example, the attenuation can include decreasing signal amplitude of nerve signals or weakening the transmission of nerve signals.

In the present example, ultrasound energy is delivered to an airway wall to attenuate nervous system signals of nerves 45 that extend along the wall of the airway 100. The ultrasound energy may be focused or unfocused and of sufficient magnitude and/or duration to affect activity of the nerve trunks 45 and attenuate the transmission of nervous system signals at the treatment site. For example, in some aspects, a treatment zone radially offset from surface tissue of the airway wall may be subjected to sufficient ultrasound energy to raise the temperature of the targeted nerve tissue beyond a threshold temperature for a selected duration which is effective in attenuating the transmission of nervous system signals. In some instances, the threshold temperature may exceed 40° C., and in some instances the threshold temperature may exceed 45° C. or 50° C. for the treatment duration. Conversely, temperatures at the surface tissue of the airway wall may be preferentially maintained below the threshold temperature by utilizing cooling techniques or other techniques described herein. In some instances, the nerve tissue in the treatment zone may be vibrated within a select frequency range to mechanically disrupt cells thereof.

FIG. 8 shows further details of a distal portion of the pulmonary treatment system 300 with it positioned within the airway 100 for a treatment procedure. More particularly, FIG. 8 provides a longitudinal side view of the treatment system 300, which is in the form of an ultrasound energy delivery assembly 310 deliverable in the airway 100 and having an elongate body 330 with a distal end portion 332 to which is mounted an expandable member 320 (e.g., expandable balloon). The ultrasound energy delivery assembly 310 is movable from a collapsed configuration (not shown) having a collapsed cross-section to an expanded configuration E having an expanded cross-section in a plane perpendicular to the longitudinal axis A. As an example, the ultrasound energy delivery assembly 310 may be moved from the collapsed configuration to the expanded configuration E by introducing fluid into an internal chamber 322 of the expandable member 320. A fluid delivery lumen 340 may be provided in the elongate body 330 for this purpose. The fluid delivery lumen 340 may be coupled in fluid communication with a fluid supply source 250 (FIG. 7). Conversely, to move the ultrasound energy delivery assembly 310 from the expanded configuration E to the collapsed configuration, fluid may be withdrawn from the internal chamber 322 of the expandable member 320. In addition to assisting in deployment of the expandable member 320, the introduced fluid may advantageously act as a coolant to provide cooling of surface airway tissue during treatment while simultaneously providing acoustic coupling for assisting in the delivering of ultrasound energy toward a treatment zone 344.

With continued reference to FIG. 8, the expandable member 320 includes a seating portion 324 that is configured to assist in locating the expandable member 320 in a desired location during treatment. The seating portion 324 may include, for example, an annular ridge or protrusion that is sized and shaped to engage surface tissue 105 of the surrounding airway 100 when the ultrasound energy delivery assembly 310 is in the expanded configuration E. The seating portion 324 is sized and shaped to preferentially seat between adjacent cartilage rings 28 in the airway 100. A size of the expandable member 320 may be selected relative to a targeted region of the airway 100 such that the seating portion 324 is at least partially embedded in the surface tissue 105 of the airway 100. The seating portion 324 may extend continuously or intermittently around all or only a portion of an outer periphery or circumference of the expandable member 320. Advantageously, the expansion of the expandable member 320 may be controlled to selectively engage the airway wall and retain the ultrasound energy delivery assembly 310 in a relatively fixed position during a treatment procedure.

The ultrasound energy delivery assembly 310 further includes an ultrasound energy emitter 350 that is configured to deliver ultrasound energy to nerve tissue spaced radially outward from surface tissue 105 of the airway 100. The ultrasound energy delivery assembly 310 includes at least one ultrasound energy delivery element 352 (e.g., ultrasound transducer) that is configured to controllably emit ultrasound pressure waves or "ultrasound energy" when driven by an excitation source 246 (FIG. 7). Examples of ultrasound energy delivery elements, excitation sources and related systems may include those shown and described in US Patent Application Publication Nos. 2010/0179424; 2012/0209118; 2012/0232436; and 2013/0197555, which are herein incorporated by reference.

In order to avoid unnecessarily obscuring descriptions of aspects of the present disclosure, well-known structures, devices, systems and methods associated with controllably emitting ultrasound energy have not been shown or described in detail. For instance, it will be appreciated that a control and processing system (e.g., controller 244 and excitation source 246) may be provided with various electrical components and communicatively coupled to the ultrasound delivery element(s) to enable functionality of the pulmonary treatment systems described herein. The control and processing system may include, for example, transmit and timing control circuitry to control waveform timing, aperture and focusing of the ultrasound energy. In addition, it will be appreciated that energy delivery elements or transducers may be utilized in a variety of shapes and sizes and may be configured to operate at various frequencies, including, for example, frequencies in the range of about 7.5 Mhz to about 20 Mhz. Again, examples of suitable ultrasound energy delivery elements, excitation sources and related systems may include those shown and described in US Patent Application Publication Nos. 2010/0179424; 2012/0209118; 2012/0232436; and 2013/0197555, which are herein incorporated by reference.

As illustrated in FIG. 8, the ultrasound energy emitter 350 is generally aligned with the seating portion 324 of the expandable member 320 such that during a treatment procedure the ultrasound energy delivery element 352 is positioned to deliver ultrasound energy in a direction toward an interface between the seating portion 324 and the surface tissue 105 of the airway 100. In this manner, the emitted ultrasound energy is directed between adjacent cartilage rings 28 of the airway 100.

In some instances, the ultrasound energy emitter 350 may include an acoustic lens 354 having a curvilinear surface profile or other focusing features to focus the ultrasound energy to the treatment zone 344, as represented by the converging path labeled 356. In this manner, ultrasound energy may be focused to cause permanent or long-term alteration to tissue located only within the treatment zone 344. A focal length of the ultrasound energy emitter 350 may be selected to target nerve tissue spaced radially outward from surface tissue 105 of the airway wall. In addition, the duration and/or intensity of the ultrasound energy may be controlled to adjust the size of the treatment zone 344. In other instances, the ultrasound energy emitter 350 may be configured to generate unfocused ultrasound energy. When generating unfocused energy, the ultrasound energy emitter 350 preferably includes an ultrasound energy delivery element 352 of sufficient size such that the target zone 344 lays entirely or at least partially within the near field or Fresnel zone. In some instances, however, the ultrasound energy delivery element 352 may be configured such the target zone 344 is located at least partially at the transition between the near field or Fresnel zone and the far field or Fraunhofer zone or beyond.

Preferably, no significant permanent or long-term tissue injury occurs at the surface tissue or in other tissues disposed radially between the target zone 344 and the ultrasound energy delivery assembly 310 as a result of the treatment procedure. In some cases, minor injury or alteration of such tissue may be permitted without having clinically significant effects. To assist in preventing or minimizing such alteration, the internal chamber 322 of the expandable member 320 may be supplied with a coolant as discussed above. The coolant also serves to provide acoustic coupling to assist in the transmission of the ultrasound energy. As illustrated in FIG. 8, the coolant may be introduced via a fluid delivery lumen 340 provided in the elongate body 330 to the internal chamber 322 of the expandable member 320. In some instances, a return lumen may also be provided to enable the circulation of coolant through the internal chamber 322.

In some treatment methods utilizing the pulmonary treatment system 300, the ultrasound energy delivery assembly 310 may be positioned and seated between a first set of adjacent cartilage rings 28 while treating a first treatment zone 344 with ultrasound energy. Subsequently, the ultrasound energy delivery assembly 310 may be unseated, rotated about longitudinal axis A and reseated between the same adjacent cartilage rings 28 or a different set of adjacent cartilage rings upstream or downstream of the first set of adjacent cartilage rings 28 for treating another treatment zone that is longitudinally and/or circumferentially displaced from the first treatment zone 344. Sequential treatments may be applied to the airway to provide full circumferential coverage of the airway. In some instances, the controller 244 and excitation source 246 (FIG. 7) may be configured to generate ultrasound energy via the ultrasound energy emitter 350 at a first power and/or frequency level for imaging purposes to assist in locating target tissue and/or positioning the ultrasound energy delivery assembly 310 relative to structures in the airway, such as, for example, the cartilage rings 28. The controller 244 and excitation source 246 (FIG. 7) may also be configured to generate ultrasound energy via the ultrasound energy emitter 350 at a second power and/or frequency for tissue ablation purposes.

In other treatment methods utilizing pulmonary treatment system 300, the ultrasound energy delivery assembly 310 may be positioned between a set of adjacent cartilage rings 28 and remain seated therebetween while rotating or pivoting the ultrasound energy emitter 350 about the longitudinal axis A, as represented by the arrow labeled 360. In such instances, the ultrasound energy emitter 350 may be coupled to a drive mechanism including a motor (not shown) and controlled to rotate or pivot about the longitudinal axis A.

In some instances, the ultrasound energy emitter 350 may include a plurality of ultrasound delivery elements 352 that are configured to generate several beams of ultrasound energy that radiate outwardly from the longitudinal axis A. In some instances, a plurality of ultrasound transducers may be circumferentially spaced about the longitudinal axis A to generate a plurality of respective beams that circumferentially overlap to provide a continuous or generally continuous beam traveling outwardly from a portion or the entire circumference of the assembly. The assembly may be configured such that a beam or plurality of beams may be emitted simultaneously to cover up to 90°, 180°, 270°, or the entire 360° of the airway circumference. In other instances, the beams may be spaced apart to radiate intermittently about the longitudinal axis A. When provided with a plurality of ultrasound delivery elements 352, the ultrasound delivery elements 352 may be excited independently of each other and may be excited simultaneously, sequentially or otherwise.

Figure 9A:
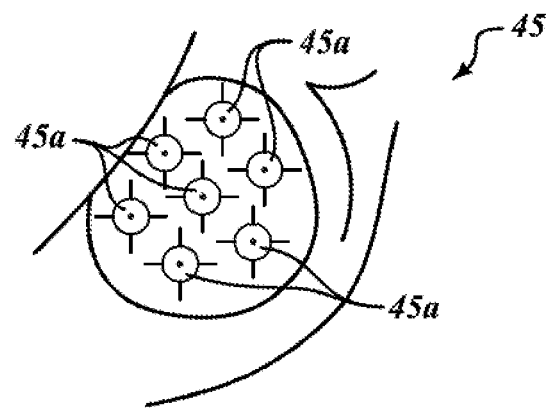
FIG. 9A is a detail view of the nerve axons of a nerve trunk associated with the airway of FIG. 9.
Figure 10A:
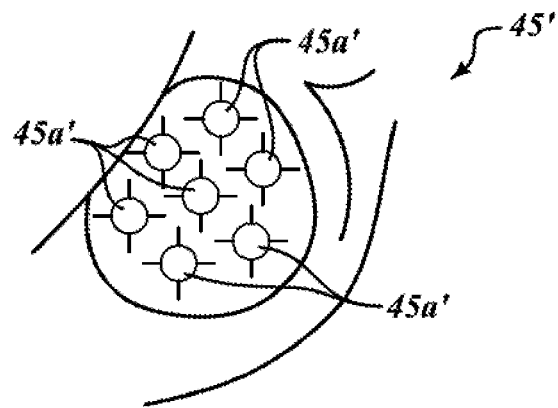
FIG. 10A is a detail view of the destroyed nerve axons of the nerve trunk associated with the airway of FIG. 10.

The effects of the example treatment described above on distal airways will now be discussed with reference to FIGS. 9-10. FIG. 9 is a cross-sectional view of a distal airway in the lung, taken along line 9-9 of FIG. 7, prior to treatment. FIG. 10 is a cross-sectional view of the same airway after treatment. FIGS. 9A and 10A provide detailed views of nerve axons 45*a* of a nerve trunk 45 associated with the distal airway before and after the treatment, respectively.

As shown in FIG. 9, prior to treatment, the lumen 101*b* of the airway 100*b* is narrow and may be partially blocked by excess mucus 150. Depending on the patient, the reduced size of the lumen 101*b* can be attributable to variety of ailments, including, for example, inflammation of the airway wall 103, constriction of the smooth muscle tissue 114, or excessive intraluminal mucus or edema fluid, or both.

Following treatment, as shown in FIG. 10, the lung lumen 101*c* has opened a significant amount, and mucus production is greatly reduced. In some instances, the increase in lumen size and/or decrease in mucus production can be attributable to nerve death at the treatment location due to, for example, absorbed ultrasound energy, and the resulting nerve death at more distal portions of the affected nerve. Under certain conditions, the absorption of ultrasound energy at the treatment location may result in loss of nerve axons distal of the treatment. For these types of treatments, it may be the case that the nerve axons that are present in the distal airways, as shown in FIG. 9A, are no longer present, as shown in FIG. 10A. Nevertheless, the function of other tissue or anatomical features, such as the mucous glands, cilia, smooth muscle, body vessels (e.g., blood vessels), and the like can be maintained even though the nerve tissue is injured.

As a result of the treatment, the nerve supply along a section of the bronchial tree can be cut off. When the signals are cut off, the distal airway smooth muscle can relax, which can lead to the airway dilation seen in FIG. 10. Cutting the nervous system signals can also causing mucous cells to decrease mucous production leading to the reduced amount of mucous in the lumen 101*c* of FIG. 10. The treatment may also cause inflammatory cells to stop producing airway wall swelling and edema. For example, the occurrence of acetylcholine receptors may be increased, while inflammatory cells, inflammatory cytokines, and other markers in the distal airway may be reduced.

All of these changes reduce airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some instances, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

In addition to the near-term benefits, interrupting nervous system signal communication with distal airways has the long term effect of remodeling previously constricted airways beyond simply relaxing the smooth muscle tissue or reducing mucous production. For example, without nervous signals causing them to contract, the smooth muscle will begin to atrophy over time. Eventually, smooth muscle and muscle gland mass will decrease. In addition, there will be a decrease in airway wall fluid, such as edema and interstitial tissue fluid. As such, unlike temporary treatments that block nervous system signals for discrete periods of time, the amount of obstruction in distal airways may continue to decrease over time following a treatment with the systems of the present disclosure.

Figure 11:
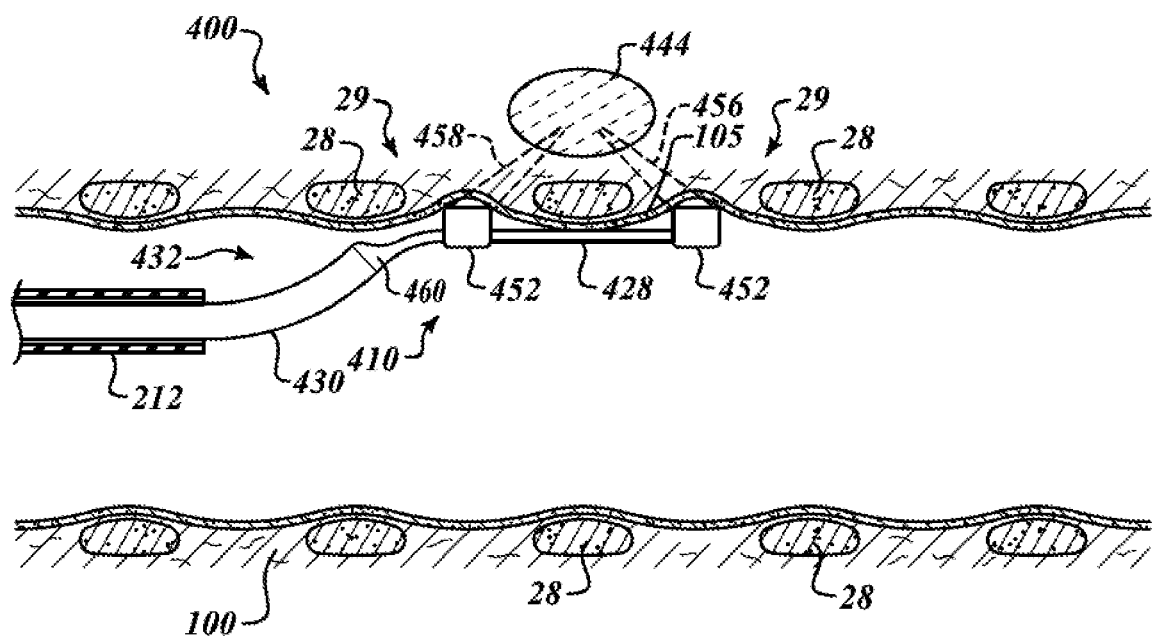
FIG. 11 is a side elevation view of a pulmonary treatment system according to another aspect.

FIG. 11 illustrates another example of a pulmonary treatment system 400, which is shown positioned within an airway 100. The pulmonary treatment system 400 is provided in the form of an ultrasound energy delivery assembly 410 which is deliverable into the airway 100 and which includes an elongate body 430 having a distal end 432. The ultrasound energy delivery assembly 410 includes at least two ultrasound delivery elements 452 (e.g., ultrasound transducers) respectively positioned to deliver energy through two different intercartilaginous spaces 29 of the airway 100 during a treatment procedure.

The energy delivery assembly 410 may include a connecting element 428 that is sized and shaped to straddle a cartilage ring 28 and position the ultrasound delivery elements 452 on respective sides thereof within the intercartilaginous spaces 29. For example, the connecting element 428 may include a seating portion having a curvilinear profile that is sized and shaped to at least partially nest with features of the surface structures of the airway wall as the ultrasound energy delivery assembly 410 is deployed and positioned for treatment. The connecting element 428 may support the ultrasound delivery elements 452 such that the ultrasound delivery elements 452 are partially embedded within surface tissue 105 of the intercartilaginous spaces 29 while the connecting element 428 abuts the airway wall in a region directly adjacent the cartilage ring 28. In other instances, the ultrasound delivery elements 452 (or adjacent seating structures) may be partially embedded within surface tissue 105 of the intercartilaginous spaces 29 while the connecting element 428 is spaced apart or offset from the airway wall in a region directly adjacent the cartilage ring 28. The adjacent cartilage rings 28 may spread slightly when the energy delivery assembly 410 is seated for treatment.

With continued reference to FIG. 11, the ultrasound energy delivery elements 452 may be oriented or otherwise configured to direct ultrasound energy to an overlapping or common treatment zone 444 when seated against or otherwise positioned near the intercartilaginous spaces 29. Each of the ultrasound delivery elements 452 may be configured to emit or generate ultrasound energy which is on its own insufficient to ablate tissue during a treatment procedure, but which may be combined within the treatment zone 444 to allow for effective denervation radially outward from surface tissue 105. In this manner, the ultrasound energy delivery elements 452 may be positioned to cooperatively generate a lesion in an area radially beyond the cartilage ring 28. Advantageously, the ultrasound delivery elements 452 (e.g., ultrasound transducers) may be respectively positioned to deliver energy through two different intercartilaginous spaces 29 of the airway 100 without repositioning the ultrasound energy delivery assembly 410. A distance or pitch between the ultrasound delivery elements 452 may be about equal to an average distance or pitch between adjacent cartilage rings 28 in the airway 100. In other instances, a distance or pitch between the ultrasound delivery elements 452 may be slightly greater than a width of the cartilage ring 28 that the ultrasound delivery elements 452 are positioned to straddle during treatment. In still further instances, a pitch or distance between the ultrasound delivery elements 452 may be adjustable.

The distal end 432 of the elongate body 430 may be configured to enable positioning of the ultrasound energy delivery elements 452 or adjacent structures of the delivery system 410 in an abutting relationship with surface tissue 105 of the airway 100. For example, the distal end 432 may be pre-shaped or biased to move toward the surface tissue 115 when deployed from a delivery sheath 212. A flexible member or joint 460 may be provided between the elongate body 430 and the ultrasound energy delivery assembly 410 to enable seating portions of the assembly 410 to conform to structures of the airway 100 as the assembly 410 is brought into contact therewith. In alternative embodiments, a positioning member such as a leaf spring, basket, or inflatable balloon may be attached to the connecting element 428 and/or ultrasound energy delivery elements 452. When deployed from delivery sheath 212, the positioning member may be configured to engage the opposing side of the airway opposite the target treatment site and urge the ultrasound energy delivery elements 452 against the airway wall. Further, acoustic coupling element(s), such as expandable balloons, may be mounted adjacent to or around the ultrasound energy delivery elements 452 to allow any space between these elements and the airway wall tissue to be filled with an acoustic coupling fluid.

In some instances, the ultrasound energy delivery assembly 410 may include an acoustic lens, a curvilinear surface profile or other focusing features (not shown in FIG. 11) to focus the ultrasound energy of each delivery element 452 to the treatment zone 444, as represented by the converging paths labeled 456, 458. In this manner, ultrasound energy may be focused to cause permanent or long-term alteration to tissue located only within the treatment zone 444. A focal length of the ultrasound delivery elements 452 may be selected to target nerve tissue spaced radially outward from surface tissue 105 and behind or radially beyond the cartilage ring 28. In addition, a focal zone of each of the ultrasound delivery elements 452 of the ultrasound energy delivery assembly 410 may be selected to overlap with each other to collectively define the treatment zone 444. In other instances, the ultrasound delivery elements 452 may be configured to generate unfocused ultrasound energy beams which overlap in the treatment zone 444. Furthermore, irrespective of the focused or unfocused nature of the emitted ultrasound energy, the duration and/or intensity of the ultrasound energy of each ultrasound delivery element 452 may be controlled to adjust the size of the treatment zone 444.

In some instances, a cooling system (not shown) may be provided to deliver coolant to an interface at which the ultrasound energy passes through the surface tissue 105 of the airway wall to reduce, minimize or eliminate the affect the focused or unfocused ultrasound energy may have on the surface tissue 105. In some embodiments, coolant may flow through one or more lumens in connecting member 428 and passages within or around ultrasound energy delivery elements 452. Alternatively, expandable balloons or bladders may be mounted adjacent to or around ultrasound energy delivery elements 452 and such balloons may be inflated with a cooled fluid. The degree of cooling may be balanced with the duration and/or intensity of the ultrasound energy that is generated by each of the delivery elements 452 to form the treatment zone 444 at a desired depth for effective denervation. Preferentially, no permanent or long-term alteration occurs at the surface tissue 105 between the target zone 444 and the ultrasound energy delivery elements 452 as a result of the treatment procedure. This may be accomplished without cooling in some embodiments. In other embodiments, cooling may be necessary to develop the desired depth of treatment while protecting surface tissue 105 from appreciable permanent or long-term alteration.

Figure 12:
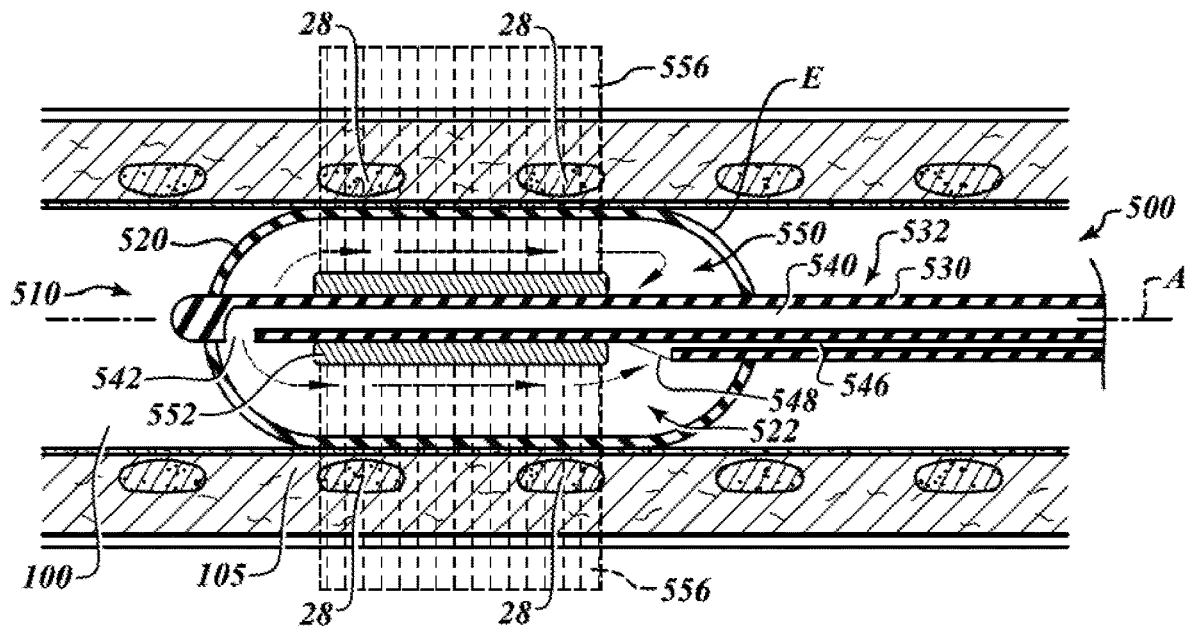
FIG. 12 is a cross-sectional view of a pulmonary treatment system according to another aspect.

FIG. 12 illustrates another example of a pulmonary treatment system 500, which is shown positioned within an airway 100. The pulmonary treatment system 500 is provided in the form of an ultrasound energy delivery assembly 510 which is deliverable into the airway 100 via a distal end 532 of an elongate body 530. The ultrasound energy delivery assembly 510 is movable from a collapsed configuration (not shown) having a collapsed cross-section in a plane transverse to longitudinal axis A to an expanded configuration E having an expanded cross-section in a plane transverse to longitudinal axis A. In order to minimize cross-sectional profile for delivery through the working lumen of a flexible bronchoscope, the collapsed cross-section of the ultrasound energy delivery assembly 510 may have a collapsed transverse dimension not more than about 6 mm, and the expanded cross-section of the ultrasound energy delivery assembly 510 may have an expanded transverse dimension of at least about 7 mm so as to contact the airway wall of the patient during treatment.

As shown in FIG. 12, the ultrasound energy delivery assembly 510 includes an ultrasound energy emitter 550 configured to delivery ultrasound energy through surface tissue 105 of the airway wall to target tissue spaced radially outward from the surface tissue 105. To facilitate the desired depth of penetration of the ultrasound energy to enable denervation of remote nerve tissue, the ultrasound energy emitter 550 may include an ultrasound delivery element 552 that includes an energy emitting portion that is at least about 7 mm in length.

In some instances, a single ultrasound delivery element 552, such as a single transducer, may be provided. In other instances, the ultrasound delivery element 552 may comprise of an array of transducers that are spaced relative to each other and mounted to a substrate which enables bending of the transducer array to facilitate delivery of the system 500 through a flexible scope or similar structure. The ultrasound delivery element(s) 552 may be configured to provide focused or unfocused ultrasound energy. As an example, the pulmonary treatment system 500 shown in FIG. 12 depicts a cylindrical transducer arrangement generating an unfocused beam of ultrasound energy, which radiates outwardly from a central axis A, as represented by the field lines labeled 556. As discussed elsewhere, cooling may be required in embodiments featuring unfocused ultrasound energy generation to protect surface tissue of the airway from appreciable alteration.

With continued reference to FIG. 12, the pulmonary treatment system 500 includes a cooling member 520 (e.g., expandable coolant chamber) that is configured to cool the surface tissue 105 while the ultrasound energy emitter 550 delivers ultrasound energy to target tissue. While this example pulmonary treatment system 500 is depicted as generating unfocused ultrasound energy, it is appreciated that in other instances, the ultrasound energy emitter 510 may include an acoustic lens or other focusing structure or feature to focus the emitted ultrasound energy. In either event, the cooling member 520 may be provided to receive coolant in a region or regions that are immediately adjacent to an interface of where the ultrasound energy passes out of the pulmonary treatment system 500 and enters surface tissue 105 during treatment procedures.

As can be appreciated in FIG. 12, coolant may be supplied to an internal chamber 522 of the coolant member 520 via a fluid supply lumen 540 and corresponding fluid inlet port 542 and discharged from the internal chamber 522 via a return lumen 546 and corresponding fluid outlet port 548. In preferred embodiments, fluid inlet port 542 is located on one end of cooling member 520 (distal end shown) while outlet port 548 is at an opposite end of cooling member 520 (proximal end shown) to allow coolant to be continuously circulated from one end of the balloon to the other during treatment. In this manner, coolant can be delivered and circulated through the internal chamber 522 to provide cooling of the surface tissue 105 that is in abutting contact with the cooling member 520. Advantageously, the coolant also provides acoustic coupling to assist in the transmission of the ultrasound energy, as well as provides a mechanism for moving the ultrasound energy delivery assembly 510 from the collapsed configuration (not shown) to the expanded configuration E shown in FIG. 12. The coolant member 522 may be compliant so as to conform closely to the surface tissue 105 during treatment and enhance acoustic coupling.

Figure 13:
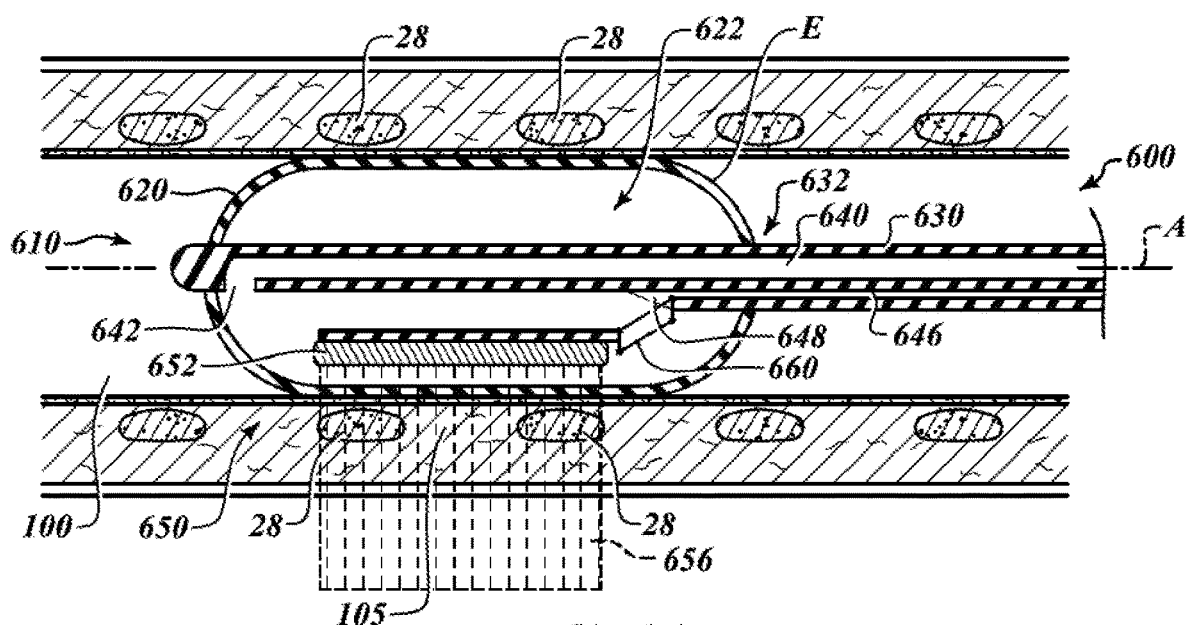
FIG. 13 is a cross-sectional view of a pulmonary treatment system according to another aspect.

FIG. 13 illustrates an example of a pulmonary treatment system 600, which is shown positioned within an airway 100. The pulmonary treatment system 600 is similar to the aforementioned system 500 of FIG. 12 and is likewise provided in the form of an ultrasound energy delivery assembly 610 which is deliverable into the airway 100 via a distal end 632 of an elongate body 630. The ultrasound energy delivery assembly 610 includes an expandable member 620 that is movable from a collapsed, delivery state (not shown) to an expanded, deployed state E and an ultrasound energy emitter 650 that is configured to delivery ultrasound energy to target nerve tissue spaced radially outward from surface tissue 105 of the airway wall. The ultrasound energy emitter 650 is positioned within the expandable member 620, but is movable radially relative to the expandable member 620 when the expandable member 620 is in the expanded, deployed state E to adjust a distance between an ultrasound energy delivery element 652 thereof and the surface tissue 105 of the airway wall. This is advantageous in enabling the ultrasound delivery element 652 to be positioned nearer to the surface tissue 105 such that the ultrasound energy has less opportunity to dissipate or be absorbed or reflected prior to reaching the target nerve tissue that is spaced radially outward from the surface tissue 105. A flexible joint 660 and control element (e.g., control wire) or other suitable mechanism (not shown) may be used adjust the position of the ultrasound delivery element 652 relative to the expandable member 620. In other instances, the ultrasound delivery element 652 may be located in a non-adjustable position at a desired offset distance from a central axis A when the system 600 is deployed and the expandable member 620 is expanded to engage the airway 100. A drive mechanism may be coupled to the ultrasound energy emitter 650 to rotate the offset ultrasound delivery element 652 about the central axis and enable circumferential treatment of the airway with the delivery element 652 in the offset position.

The expandable member 620 of the pulmonary treatment system 600 of FIG. 13 may also serve as cooling chamber that is configured to cool the surface tissue 105 while the ultrasound energy emitter 650 delivers ultrasound energy to target tissue. While this example pulmonary treatment system 600 is depicted as generating unfocused ultrasound energy, as indicated by field lines 656, it is appreciated that in other instances, the ultrasound energy emitter 650 may include an acoustic lens or other focusing structure or feature to focus the emitted ultrasound energy.

As can be appreciated in FIG. 13, coolant may be supplied to an internal chamber 622 of the coolant member 620 via a fluid supply lumen 640 and corresponding fluid inlet port 642 and discharged from the internal chamber 622 via a return lumen 646 and corresponding fluid outlet port 648. In this manner, coolant can be delivered and circulated through the internal chamber 622 to provide cooling of the surface tissue 105 that is in abutting contact with the expandable member 620. Advantageously, the coolant also provides acoustic coupling to assist in the transmission of the ultrasound energy, as well as provides a mechanism for moving the ultrasound energy delivery assembly 610 from the collapsed state (not shown) to the expanded state E shown in FIG. 13.

Figure 14:
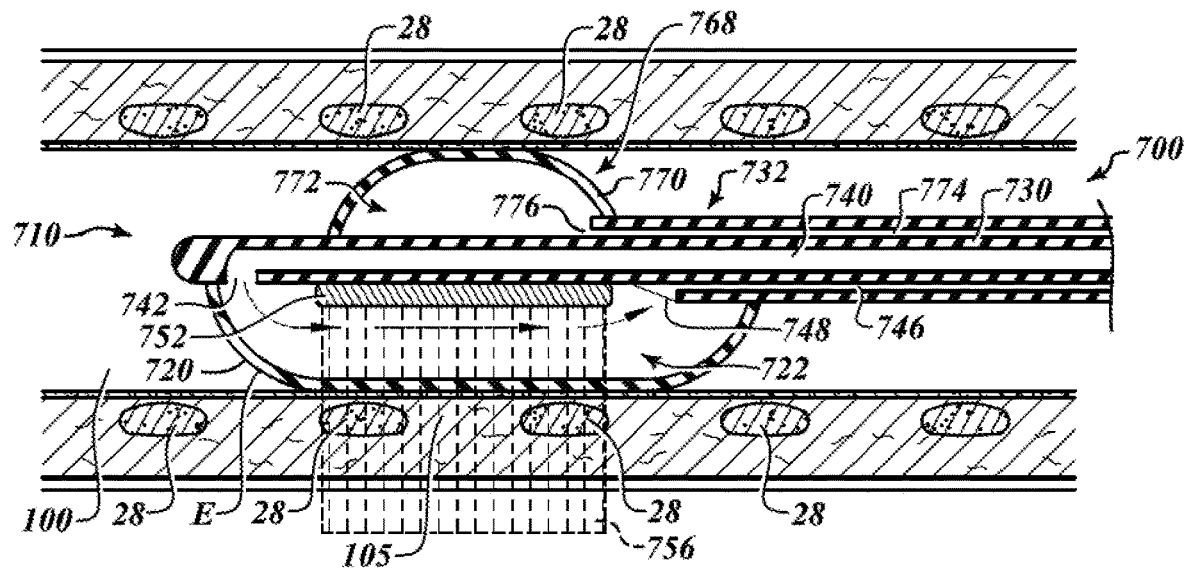
FIG. 14 is a cross-sectional view of a pulmonary treatment system according to another aspect.
Figure 15:
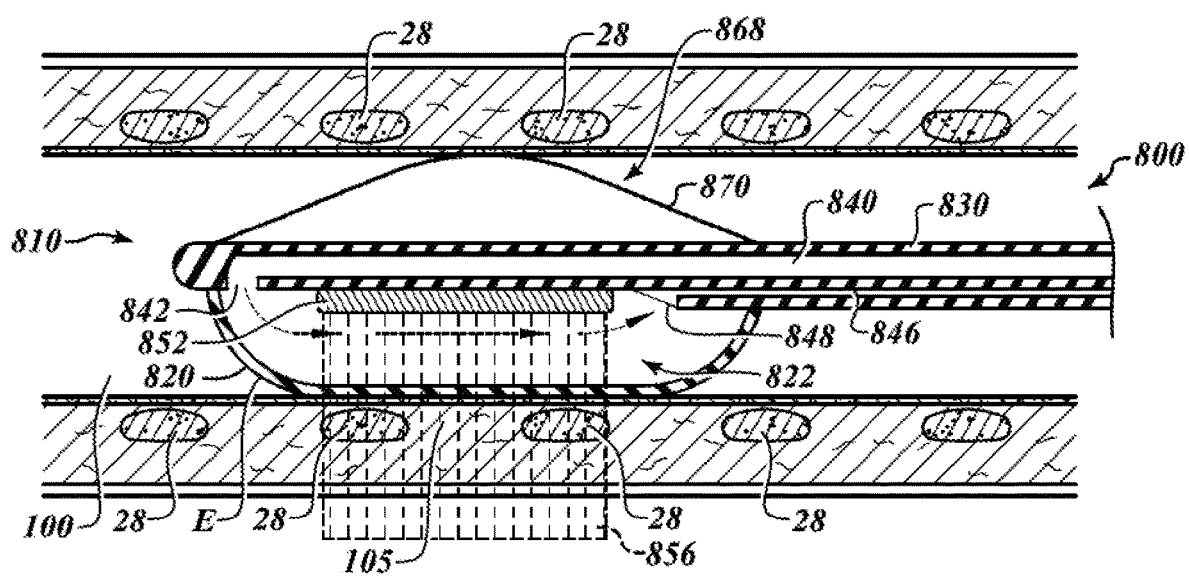
FIG. 15 is a cross-sectional view of a pulmonary treatment system according to another aspect.
Figure 16:
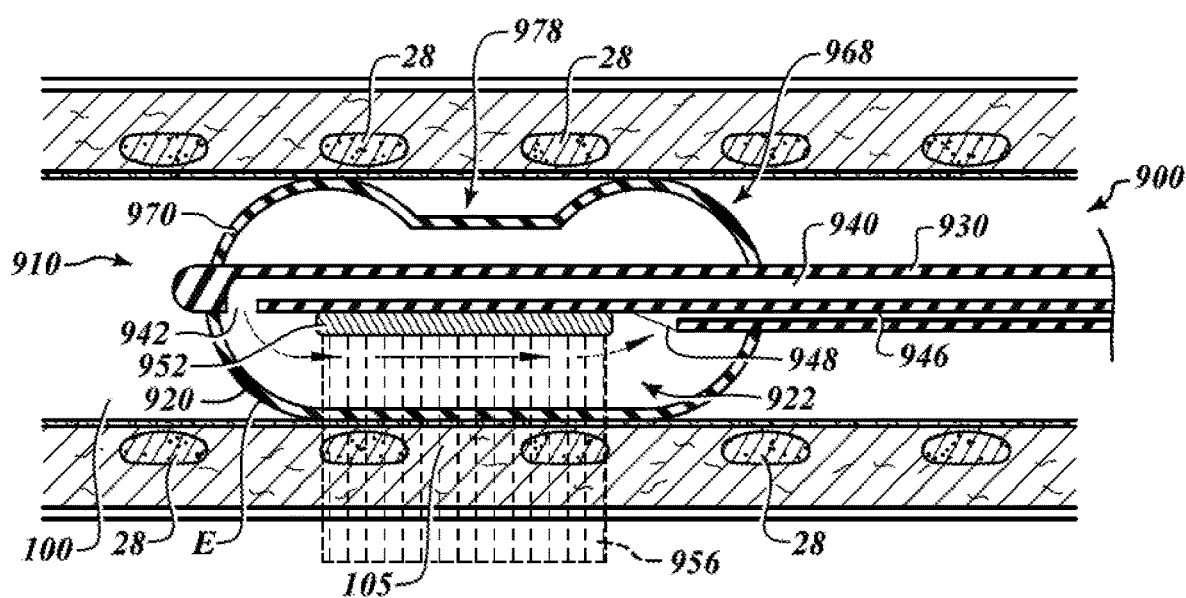
FIG. 16 is a cross-sectional view of a pulmonary treatment system according to another aspect.

FIGS. 14-16 illustrate further examples of pulmonary treatment systems 700, 800, 900, which are each shown positioned within an airway 100. Each pulmonary treatment system 700, 800, 900 is provided in the form of an ultrasound energy delivery assembly 710, 810, 910 which is deliverable into the airway 100 via a distal end 732, 832, 932 of an elongate body 730, 830, 930. Each ultrasound energy delivery assembly 710, 810, 910 includes an expandable member 720, 820, 920 that is configured to cool the surface tissue 105 while the ultrasound energy delivery assembly 710, 810, 910 delivers ultrasound energy to target nerve tissue. While these example pulmonary treatment systems 700, 800, 900 are each depicted as generating unfocused ultrasound energy, as represented by field lines 756, 856, 956, it is appreciated that in other instances, the ultrasound energy delivery assembly 710, 810, 910 may include an acoustic lens or other focusing structure or feature to focus the emitted ultrasound energy. In either event, the expandable member 720, 820, 920 may be provided to receive coolant at least in a region or regions that are immediately adjacent to an interface of where the ultrasound energy passes out of the pulmonary treatment system 700, 800, 900 and enters surface tissue 105 during a treatment procedure.

As can be appreciated in FIGS. 14-16, coolant may be supplied to an internal chamber 722, 822, 922 of the expandable member 720, 820, 920 via a fluid supply lumen 740, 840, 940 and corresponding fluid inlet port 742, 842, 942 and discharged from the internal chamber 722, 822, 922 via a return lumen 746, 846, 946 and corresponding fluid outlet port 748, 848, 948. In this manner, coolant can be delivered and circulated through the internal chamber 722, 822, 922 to provide cooling of the surface tissue 105 that is in abutting contact with the expandable member 720, 820, 920. Advantageously, the coolant also provides acoustic coupling to assist in the transmission of the ultrasound energy, as well as provides a mechanism for moving the ultrasound energy delivery assembly 710, 810, 910 from the collapsed configuration (not shown) to the expanded configuration E shown in FIGS. 14-16.

Each pulmonary treatment system 700, 800, 900 may further include a biasing element 768, 868, 968 arranged to urge the expandable member 720, 820, 920 away from a non-treatment side of the airway wall. With reference to FIG. 14, the biasing element 768 may be provided in the form of a supplemental expandable member 770 having an internal chamber 772 that is in fluid communication with a supply lumen 774 and corresponding port 776. The supplemental expandable member 770 may be inflated or otherwise pressurized independently of the primary expandable member 720 to contact the non-treatment side of the airway wall and urge the primary expandable member 720 away from the non-treatment side. A magnitude of the bias may be selected to press the expandable member 720 into secure abutting contact with the airway wall on the treatment side. Advantageously, the ultrasound energy delivery assembly 710 can readily adapt to different sized airways by adjusting the amount of fluid introduced into the internal chamber 772 of the supplemental expandable chamber 770. Moreover, the supplemental expandable member 770 may be filled with air or another fluid that acts as an effective barrier or shield to ultrasound energy that may be directed or reflected toward the non-treatment side.

With reference to FIG. 15, the biasing element 868 may be provided in the form of a spring 870, a partial expandable basket or other resilient or elastically deformable member. Again, the magnitude of the bias may be selected to press the expandable member 820 into secure abutting contact with the airway wall on the treatment side.

With reference to FIG. 16, the biasing element 968 may be provided in the form of an asymmetrical portion 970 of the expandable member 920. Asymmetrical portion 970 is configured such that, when expandable member 920 is expanded, ultrasound energy delivery element 952 is positioned closer to the treatment side of the airway than the non-treatment side. In one embodiment, expandable member 920 is mounted to elongate body 930 in a radially offset manner so as to have a greater volume on one lateral side of elongate body 930 than the other. In addition, the expandable member 920 may be shaped to include an air gap 978 between expandable member 920 and the airway wall when the ultrasound energy delivery assembly 910 is seated or otherwise positioned for treatment. In the embodiment shown, expandable member 920 has a pair of axially-offset bulges, separated by a region of smaller diameter, thus providing an air gap between the bulges. When provided, the air gap 978 may act as an effective barrier or shield to ultrasound energy that may be directed or reflected toward the non-treatment side during the treatment procedure.

Figure 17:
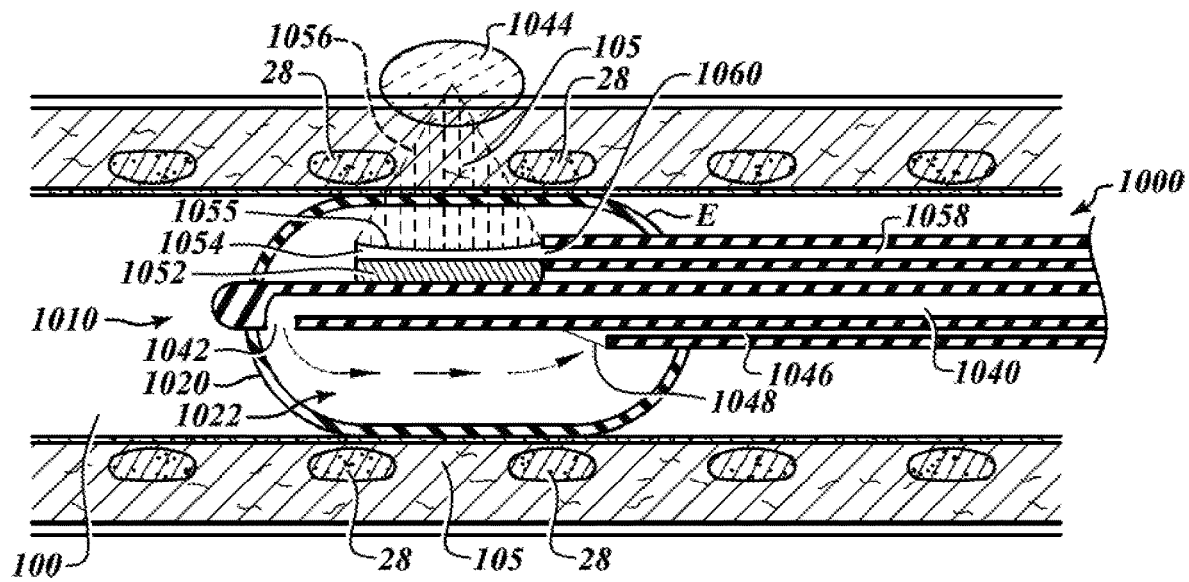
FIG. 17 is a cross-sectional view of a pulmonary treatment system according to another aspect.
Figure 18:
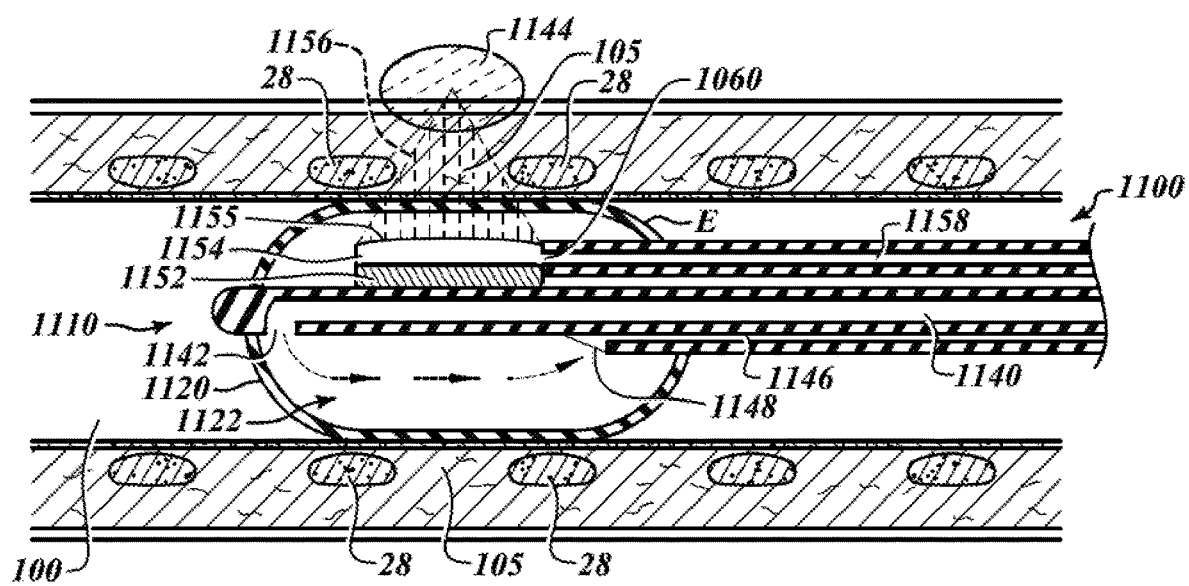
FIG. 18 is a cross-sectional view of a pulmonary treatment system according to another aspect.

FIGS. 17-18 illustrate yet further examples of pulmonary treatment systems 1000, 1100, which are each shown positioned within an airway 100. Each pulmonary treatment system 1000, 1100 is provided in the form of an ultrasound energy delivery assembly 1010, 1110 which is deliverable into the airway 100 via a distal end of an elongate body. Each ultrasound energy delivery assembly 1010, 1110 includes an expandable member 1020, 1120 that is configured to cool surface tissue 105 while the ultrasound energy delivery assembly 1010, 1110 delivers ultrasound energy to target nerve tissue. Each ultrasound energy delivery assembly 1010, 1110 of FIGS. 17 and 18 further includes an acoustic lens 1054, 1154 to focus ultrasound energy emitted from an ultrasound delivery element 1052, 1152 received within the expandable member 1020, 1120. The ultrasound delivery element 1052, 1152 and acoustic lens 1054, 1154 may be configured to focus ultrasound energy between adjacent cartilage rings 28 and at a treatment zone 1044, 1144 radially offset from surface tissue 105 of the airway wall, as represented by the field lines labeled 1056, 1156. The expandable member 1020, 1120 may be provided to receive coolant at least in a region or regions that are immediately adjacent to an interface of where the ultrasound energy passes out of the pulmonary treatment system 1000, 1100 and enters surface tissue 105 during a treatment procedure.

As illustrated in FIGS. 17 and 18, coolant may be supplied to an internal chamber 1022, 1122 of the expandable member 1020, 1120 via a fluid supply lumen 1040, 1140 and corresponding fluid inlet port 1042, 1142 and discharged from the internal chamber 1022, 1122 via a return lumen 1046, 1146 and corresponding fluid outlet port 1048, 1148. In this manner, coolant can be delivered and circulated through the internal chamber 1022, 1122 to provide cooling of the surface tissue 105 that is in abutting contact with the expandable member 1020, 1120. Advantageously, the coolant also provides acoustic coupling to assist in the transmission of the ultrasound energy, as well as provides a mechanism for moving the ultrasound energy delivery assembly 1010, 1110 from the collapsed configuration (not shown) to the expanded configuration E shown in FIGS. 17 and 18.

As illustrated in FIGS. 17 and 18, lens fluid may be supplied to the acoustic lens 1054, 1154 via a fluid supply lumen 1058, 1158 and corresponding fluid port 1060, 1160. In this manner, lens fluid can be selectively delivered to the lens to provide focusing of the emitted ultrasound energy. For example, dissimilar fluids having different acoustic impedance characteristics can be delivered to the lens 1054, 1154 and the expandable member 1020, 1120, respectively, to create a boundary at which the ultrasound energy may be redirected. In some instances, a surface 1055, 1155 of the lens 1054, 1154 may be selected to include a predefined shape at said boundary that assists in focusing the emitted ultrasound energy. The predefined boundary may include, for example, a convex or concave curvilinear surface as shown in FIGS. 17 and 18.

Figure 19:
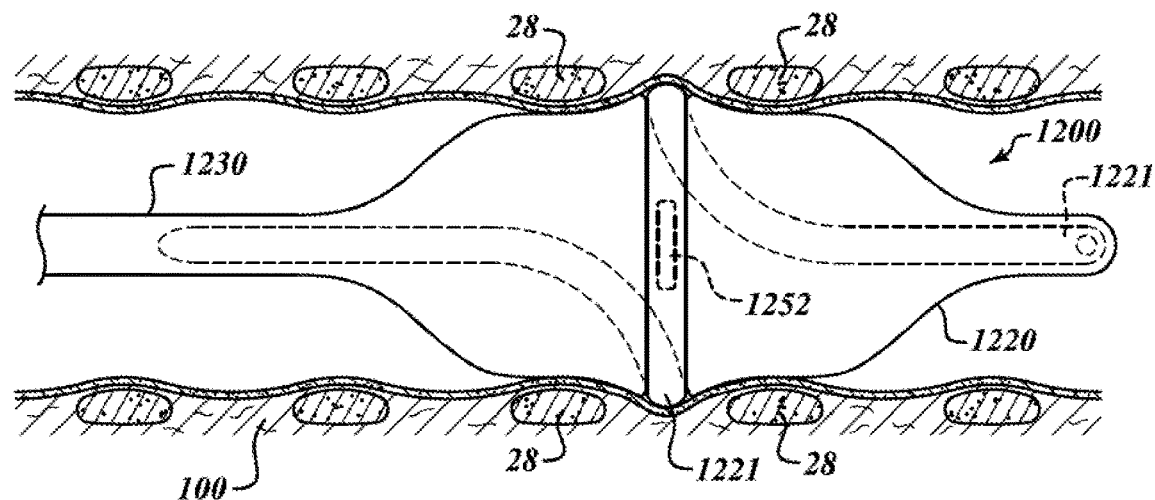
FIG. 19 is a side elevation view of a pulmonary treatment system according to another aspect.

FIG. 19 is a side elevation view of a distal portion of a pulmonary treatment system 1200 in a fully deployed state, according to another aspect. The pulmonary treatment system 1200 includes an expandable member 1220 that extends from a distal end of an elongate member 1230. The elongate member 1230 preferentially includes a supply lumen and a return lumen extending therethrough. A liquid coolant supply channel 1221 also extends from the distal end of the elongate member 1230, around a portion of the circumference of the expandable member 1220, to a distal end of the expandable member 1220. A proximal end of the liquid coolant supply channel 1221 is in fluid communication with the supply lumen, and a distal end of the liquid coolant supply channel 1221 is in fluid communication with the interior of the expandable member 1220. The return lumen is in fluid communication with the interior of the expandable member 1220 at a proximal end of the expandable member 1220. An ultrasound energy delivery device 1252 is positioned within the liquid coolant supply channel 1221. Alternatively, the ultrasound energy delivery device 1252 may be positioned on the exterior surface of the liquid coolant supply channel 1221. In either case, the ultrasound energy delivery device 1252 is movable from a generally axially extending position prior to inflation of the expandable member 1220 to a generally circumferentially extending direction upon inflation. Advantageously, the ultrasound energy delivery device 1252 may be brought into direct contact with or relatively close proximity to the wall of the airway 100 during treatment.

A liquid coolant is circulated through the pulmonary treatment system 1200 during energy delivery. For example, a liquid coolant is circulated serially from the supply lumen, through the liquid coolant supply channel 1221, into the expandable member 1220, and then out the return lumen. Liquid coolant circulating through the liquid coolant supply channel 1221 and the expandable member 1220 protect a region of tissue between an interior wall of an airway and a target treatment region that is located within the airway wall and radially spaced from the interior wall of the airway. In order to protect a region of tissue between an interior wall of an airway and a target treatment region that is located within the airway wall and radially spaced from the interior wall of the airway, it is desirable in some examples, to remove about 0.1 to 0.4 W/mm$^2$ from the airway wall during activation of the ultrasound energy delivery element 1252 by circulating a coolant through the liquid coolant supply channel 1221 and the expandable member 1220. In other examples, between about 0.025 and about 1.0 W/mm$^2$ of heat energy may be removed from the airway wall during treatment.

Figure 20:
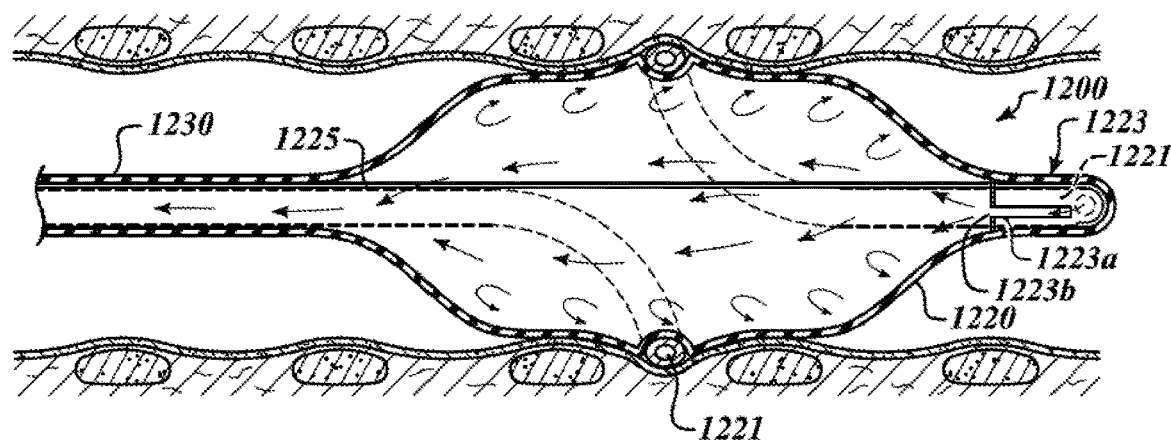
FIG. 20 is a cross-sectional view of a pulmonary treatment system according to another aspect.

FIG. 20 is a cross-sectional view of the pulmonary treatment system 1200, having a different configuration of throttle between the liquid coolant supply channel 1221 and the expandable member 1220. A throttle 1223 is provided and includes a channel 1223*a* that leads to a single, restrictive opening 1223*b* between the liquid coolant supply channel 1221 and the expandable member 1220. In one non-limiting example, the opening 1223*b* is about 0.26" in diameter. The pressure differential created by the throttle 1223 can be significant, creating a pressure differential of at least 20 psi with values greater than 50 psi on the liquid coolant supply channel 1221 side, and less than 30 psi on the expandable member 1220. In another example, the pressure differential is at least 45 psi with coolant pressure greater than 60 psi on the liquid coolant supply channel 1221 side, and less than 15 psi on the expandable member 1220 side. In one example, the pressure differential is at least 72 psi, with pressure approximately 75 psi on the liquid coolant supply channel 1221 side, and approximately 3 psi on the expandable member 1220 side.

It has been recognized that inducing turbulent flow along the surface of the expandable member 1220 improves the efficiency with which the expandable member 1220 transports heat away from an airway wall at a treatment site. In addition to creating a pressure differential in the coolant supply system, the throttle of the pulmonary treatment system 1200 can be configured to improve coolant flow in the expandable member 1220, and thereby improve the cooling efficacy of the expandable member 1220. The position, orientation, and/or shape of the throttle 1223 can be configured to induce eddies and turbulent flow along the surface of the expandable member 1220, which improves the efficiency with which the expandable member 1220 transports heat away from an airway wall of the patient at a treatment site. For example, the opening 1223*a* in the throttle 1223 creates a Jacuzzi jet effect throughout the expandable member 1220, thereby improving heat transport and cooling efficiency of the expandable member 1220.

In another aspect, a gas may be injected into the liquid coolant supply. The injected gas generates bubbles in the expandable member 1220 that disrupt laminar flow along the walls of the expandable member 1220 and thereby improve the efficiency with which heat is transported from the portion of the expandable member 1220 in contact with airway tissue at the treatment site.

In another example, the expandable cooling member 1220 includes a small, longitudinally extending, axial support 1225. In the example of FIG. 20, the support 1225 is a centrally located axial shaft that includes a shape memory material. The axial support 1225 can aid in pushability of the expandable member 1220 while allowing the expandable member 1220 to be formed of a lightweight, highly compliant material.

Figure 21:
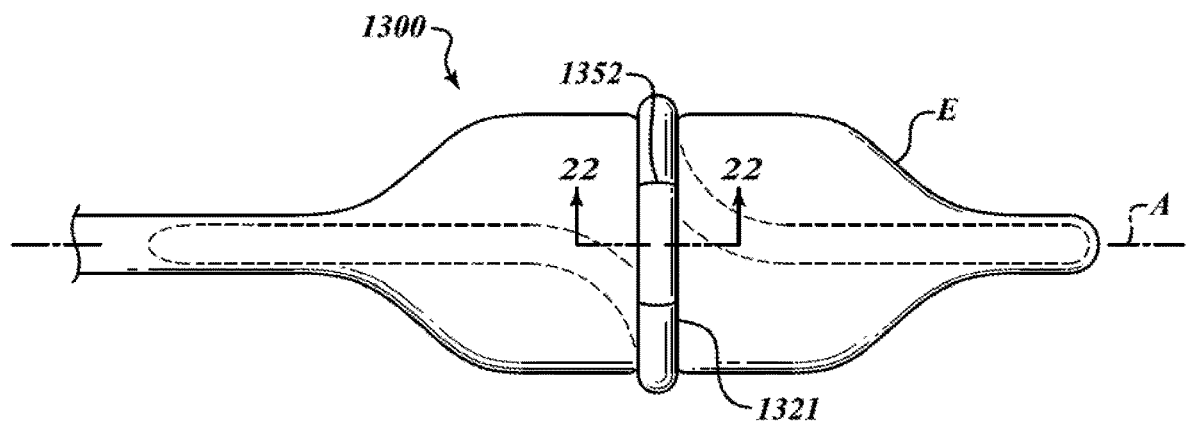
FIG. 21 is a side elevation view of a pulmonary treatment system according to another aspect.
Figure 22:
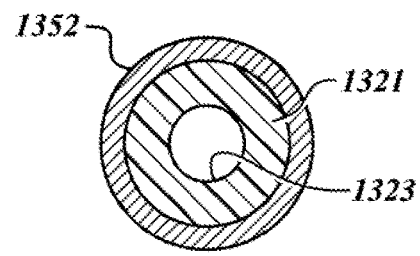
FIG. 22 is a cross-sectional view of an ultrasound delivery element and fluid delivery conduit of the pulmonary treatment system of FIG. 21, taken along line 22-22.

FIG. 21 illustrates an example of a pulmonary treatment system 1300 in fully expanded state E, and FIG. 22 provides a cross-sectional view of an ultrasound energy delivery element 1352 thereof and a liquid coolant supply channel 1321 in a semi-rigid or rigid state with a fluid supply lumen 1323 for passage of liquid coolant. In this expanded state E, the liquid coolant supply channel 1321 is sized and dimensioned to extend circumferentially around an interior wall of the patient's airway with the ultrasound energy delivery element 1352 aligned generally parallel to a portion of liquid coolant supply channel 1321 and generally perpendicular to a longitudinal axis A of the pulmonary treatment system 1300.

With continued reference to FIGS. 21 and 22, the ultrasound energy delivery element 1352 may partially or completely surround the liquid coolant supply channel 1321. Moreover, although one ultrasound energy delivery element 1352 is shown, it is appreciated that a series or plurality of ultrasound energy delivery elements 1352 may be positioned along or within the liquid coolant supply channel 1321. The ultrasound energy delivery elements 1352 may be positioned along or within the liquid coolant supply channel 1321, for example, to generate intermittent lesions about the circumference of the airway 100 radially offset from surface tissue of the airway 100. In addition, although the ultrasound energy delivery element 1352 and corresponding portion of the liquid coolant supply channel 1321 are shown extending generally perpendicular to a longitudinal axis A of the pulmonary treatment system 1300, it is appreciated that in other instances, the ultrasound energy delivery element 1352 and corresponding portion of the liquid coolant supply channel 1321 may be aligned at an angle or skewed relative to the longitudinal axis A. In addition, the position and orientation of the ultrasound energy delivery element 1352 and corresponding portion of the liquid coolant supply channel 1321 may move when moving from a stowed stated to the expanded state E.

Figure 23:
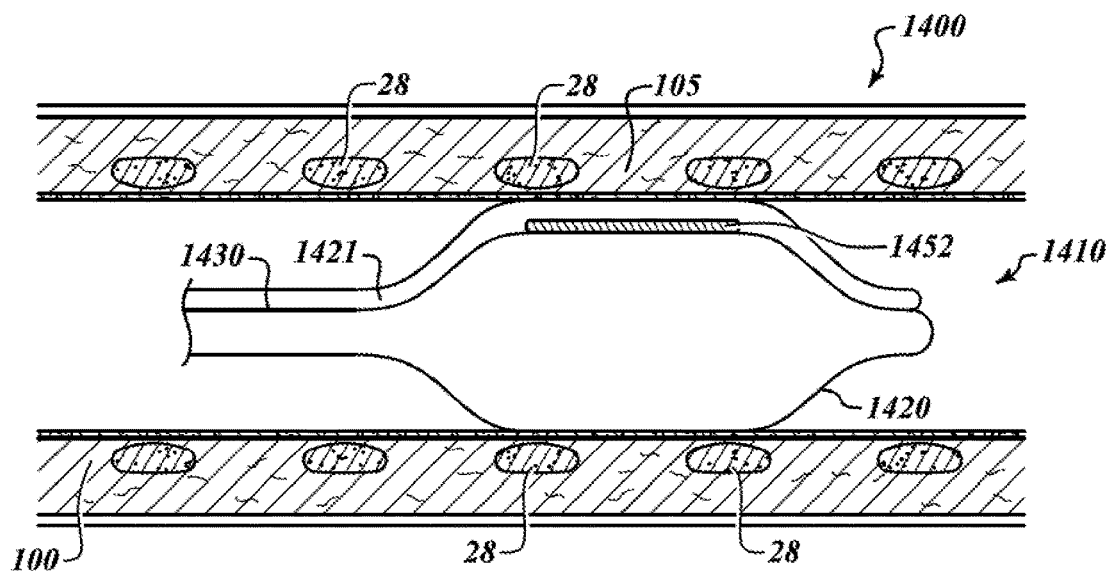
FIG. 23 is a side elevation view of a pulmonary treatment system according to another aspect.

FIG. 23 shows another example of a pulmonary treatment system 1400 having an ultrasound energy delivery assembly 1410 coupled to a distal end of an elongate body 1430 and being positionable into an airway 100 of a patient. The ultrasound energy delivery assembly 1410 is movable from a collapsed configuration (not shown) to an expanded configuration E. The ultrasound energy delivery assembly includes an apposition member 1420, a fluid conduit 1421 that extends along an exterior of the apposition member 1420, and an ultrasound energy delivery element 1452 positioned along the fluid conduit 1421 which is configured to deliver ultrasound energy to target nerve tissue spaced radially outward from surface tissue 105 of the airway wall. The apposition member 1420 may be an inflatable balloon or other expandable member (e.g., expandable basket structure) that is configured to bring the fluid conduit 1421 in contact with the airway wall during delivery of ultrasound energy to the target nerve tissue.

In some instances, an ultrasound delivery element 1452 may be positioned within the fluid conduit 1421. In other instances, the delivery element 1452 may be positioned outside of the fluid conduit 1421 between the fluid conduit 1421 and the apposition member 1420. The fluid conduit 1421 may extend longitudinally along the exterior of the apposition member 1420 and the ultrasound delivery element 1452 may extend parallel to the fluid conduit 1421. Alternatively, the fluid conduit 1421 may extend at a nonlongitudinal angle, in a helical arrangement, or in a circumferential arrangement on the apposition member 1420. The ultrasound delivery element 1452 may be completely or substantially concealed between the fluid conduit 1421 and apposition member 1420. Fluid may circulate through a longitudinal length of the fluid conduit 1421 to provide enhanced cooling of tissue abutting the same during treatment procedures. The fluid in the fluid conduit 1421 may also advantageously serve as a coupling fluid to assist in transmitting ultrasound energy through the fluid conduit 1421 into adjacent surface tissue 105 and ultimately a treatment site radially offset from the surface tissue 105. In some instances, the fluid conduit 1421 may be positioned within the apposition member 1420, such as, for example, adjacent an interior surface of the apposition member 1420. The fluid conduit 1421 and the apposition member 1420 may be integrally formed. In other instances, the fluid conduit 1421 and the apposition member 1420 may be formed separately and coupled and/or positioned together.

Figure 24:
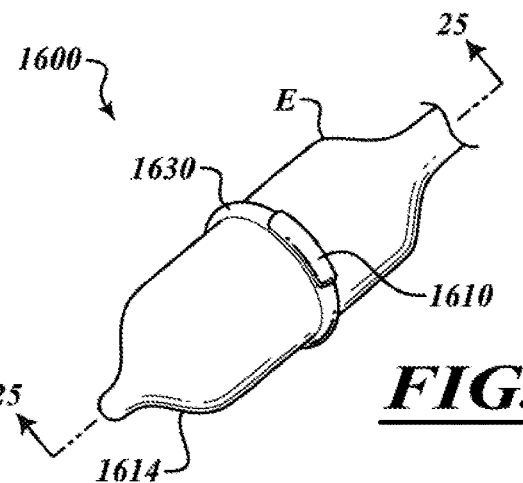
FIG. 24 is an isometric view of a pulmonary treatment system according to another aspect.
Figure 25:
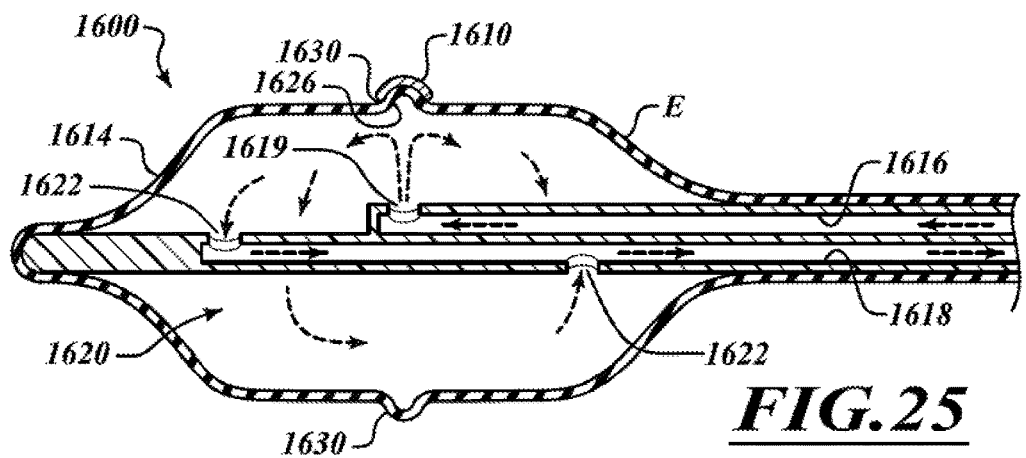
FIG. 25 is a cross-sectional view of the pulmonary treatment system of FIG. 24 taken along line 25-25.

FIGS. 24 and 25 show a pulmonary treatment system 1600 having an open cooling channel 1626 in communication with a chamber of an expandable member 1614. An ultrasound transducer 1610 is mounted to the exterior of expandable member 1614. An annular rib or protrusion 1630 can be formed in the wall of expandable member 1614, and the ultrasound transducer 1610 or a mounting substrate coupled thereto may have a curved cross-sectional shape which nests over the annular rib to help maintain the position of the ultrasound transducer 1610 and to create greater surface area for heat transfer between the expandable member 1614 and the ultrasound transducer 1610. Coolant can be delivered through a delivery lumen 1616. The coolant passes through a port 1619 into an internal chamber 1620 of the expandable member 1614. The port 1619 is configured to direct the coolant towards a region of the ultrasound transducer 1610 in the form of a stream or jet to cool the region. The coolant circulates and exits the chamber 1620 via ports 1622. The coolant flows proximally along a return lumen 1618. To enhance cooling capabilities, the flow of coolant is aimed and delivered towards the region of the ultrasound transducer 1610. Advantageously, coolant may be supplied directly towards the region of the ultrasound transducer 1610 and immediately adjacent portions of the expandable member 1614 located proximally and distally to the ultrasound transducer 1610 to cool surface tissue 105 at or near the interface where the ultrasound transducer 1610 is brought into contact with the airway wall during treatment. The ultrasound transducer 1610 may have an elongated shape which is aligned generally transverse to the expandable member 1614 when the expandable member 1614 is in the expanded configuration E shown in FIGS. 24 and 25.

Figure 26:
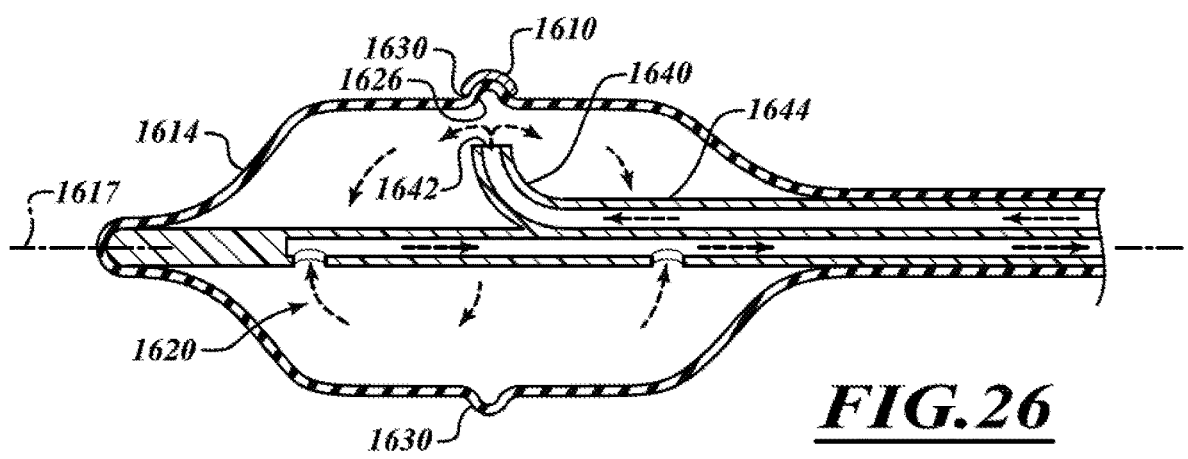
FIG. 26 is a cross-sectional view of a pulmonary treatment system according to another aspect.

As shown in FIG. 26, a variation of the pulmonary treatment system 1600 discussed above may be provided with a delivery conduit 1644 that has a tip 1640 that extends laterally away from a longitudinal axis 1617 towards the ultrasound transducer 1610 such that an outlet port 1642 is positioned in close proximity to ultrasound transducer 1610. Coolant can exit the port 1642 and flow directly toward the region of the ultrasound transducer 1610 to maximize cooling thereof and immediately adjacent portions of the expandable member 1614 located proximally and distally to the ultrasound transducer 1610 to cool surface tissue 105 at or near the interface where the ultrasound transducer 1610 is brought into contact with the airway wall during treatment.

Figure 27:
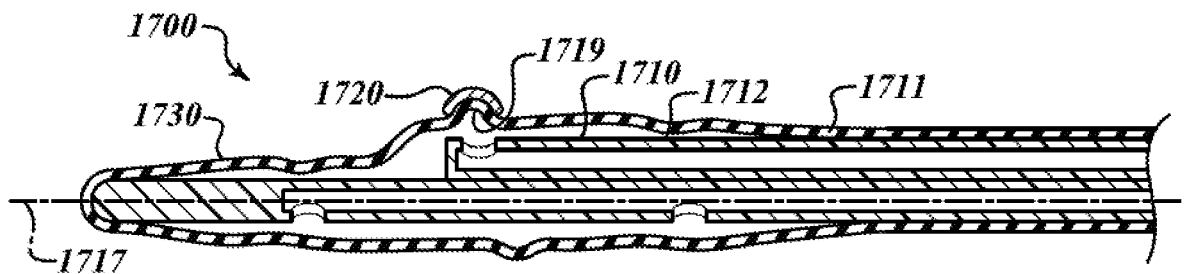
FIG. 27 is a cross-sectional view of a pulmonary treatment system according to another aspect having an actuatable delivery conduit.
Figure 28:
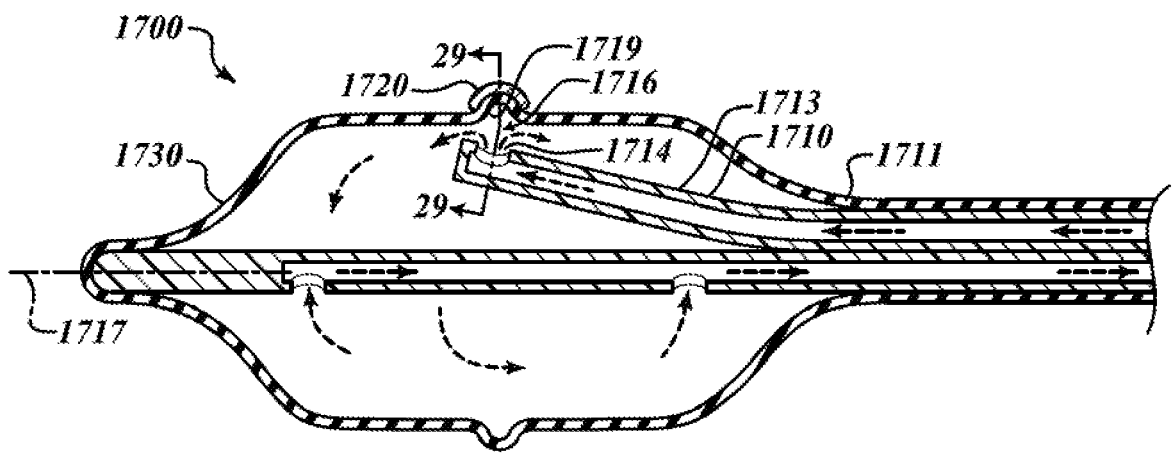
FIG. 28 is a cross-sectional view of the pulmonary treatment system of FIG. 27 in a deployed configuration.

FIG. 27 shows an example of a pulmonary treatment system 1700 having a deflectable delivery conduit 1710 coupled to an elongate body 1711 and movable from a axially-aligned delivery position 1712 to a deployed position 1713 radially offset from elongate body 1711, as shown in FIG. 28. The delivery conduit 1710 is resiliently biased into the deployed position 1713 in which it is closer to the inner wall of expandable member 1730 in its inflated configuration. In one embodiment, deflated expandable member 1730 (e.g., a deflated balloon) can hold the delivery conduit 1710 in the straight configuration until the expandable member 1730 is inflated. Both the expandable member 1730 and the biased delivery conduit 1710 can be deployed together. In other instances, the delivery conduit 1710 may be made of a shape memory material that moves when activated. For example, the delivery conduit 1710 can move from the delivery position 1712 to the deployed position 1713 when heated.

Figure 29:
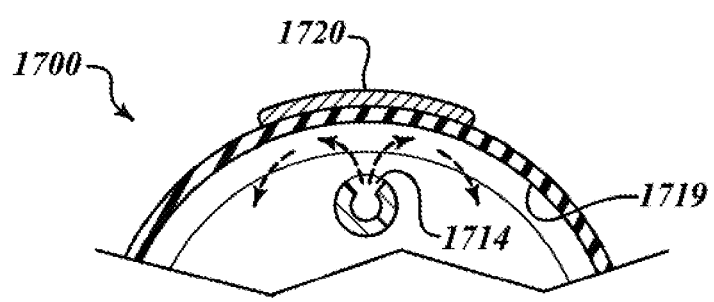
FIG. 29 is a partial cross-sectional view of the pulmonary treatment system of FIG. 28 taken along line 29-29.

With reference to FIG. 29, in the deployed configuration, a coolant port 1714 of the delivery conduit 1710 is closer to the ultrasound transducer 1720 (and the underlying cooling channel 1719) than to a longitudinal axis 1717 (FIGS. 27 and 28) of the pulmonary treatment system 1700. A fluid jet flows out of the port 1714 and into the channel 1719. The coolant can flow along the entire length and width of the ultrasound transducer 1720 to provide generally uniform cooling in the region adjacent the ultrasound transducer 1720, including immediately adjacent portions of the expandable member 1730 located proximally and distally to the ultrasound transducer 1720. When the expandable member 1730 is deflated, the delivery conduit 1710 is moved back to a generally midline position.

Figure 30:
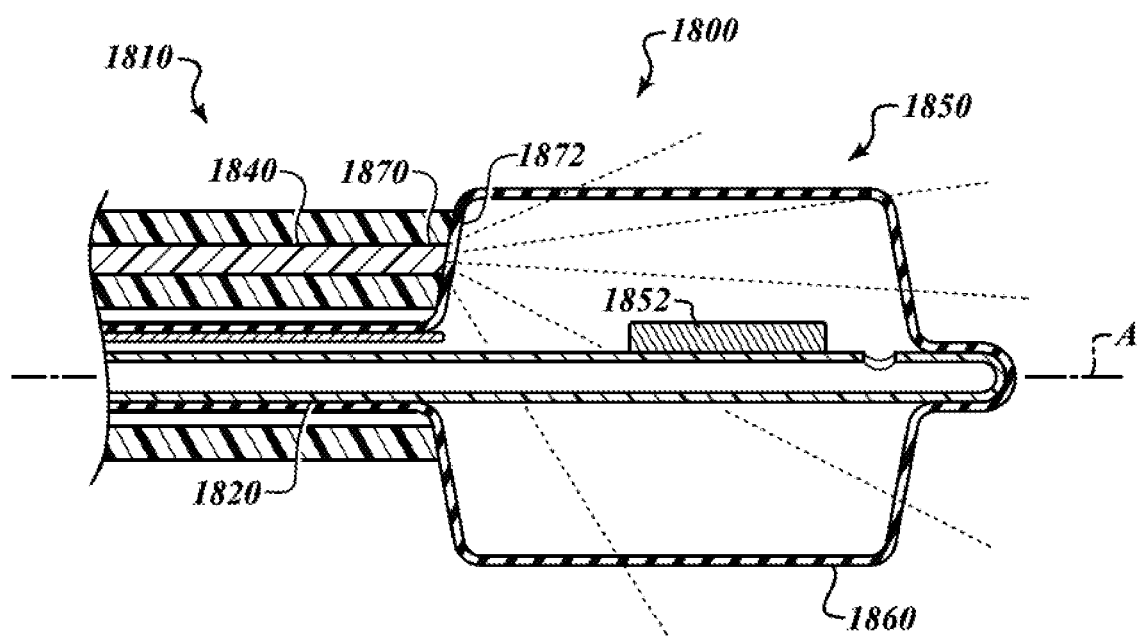
FIG. 30 is a cross-sectional view of a pulmonary treatment system according to another aspect.

FIG. 30 shows a pulmonary treatment system 1800 including an ultrasound energy delivery assembly 1810, according to another aspect. An elongate body 1820 extends through a working lumen 1830 of an ultrasound energy delivery assembly 1810. An optical element 1840 can be used to view and position an ultrasound energy emitting assembly 1850 thereof, and more particularly the position and orientation of an ultrasound energy delivery element 1852 (e.g., ultrasound transducer) of the emitting assembly 1850. An expandable member 1860 which surrounds and encloses the ultrasound energy delivery element 1852 can be transparent or semi-transparent.

The ultrasound energy delivery assembly 1810 may be or include a bronchoscope with camera optics 1840. A distal end 1870 of the camera optics 1840 is optically coupled to a wall 1872 of the expandable member 1860. The distal end 1870 can be pressed against the conformable expandable member's proximal surface to provide optical coupling. During use, the user may view the ultrasound energy delivery element 1852 or other components or anatomical features through the wall 1872 of the expandable member 1860 and fluid within the expandable member 1860.

In other embodiments, the delivery assembly 1810 can be or include a sheath with fiber optics 1840 having lenses, light sources, cameras, or the like. In certain embodiments, the optical element 1840 is integrated or coupled to the expandable member 1860. This can prevent mucous or other unwanted substances from obscuring the user's view. The geometry of the expandable member, specifically the angle of the proximal wall 1872 of the expandable member 1860, may be selected to optimize optical coupling with the camera optics 1840. The proximal wall 1872 can have a section which can be aligned with the camera optics 1840 and which is substantially flat, smooth, transparent, and which is parallel to the plane of the distal end 1870 of the camera optics 1840, preferably in some embodiments being disposed at an angle of about 75 degrees to about 105 degrees relative to the longitudinal axis A of the elongate body 1820. The material of the proximal wall 1872 may be selected to optimize visibility and transparency, e.g., with a refractive index which is compatible with the camera optics 1840 and/or fluid within the expandable member 1860.

Figure 31:
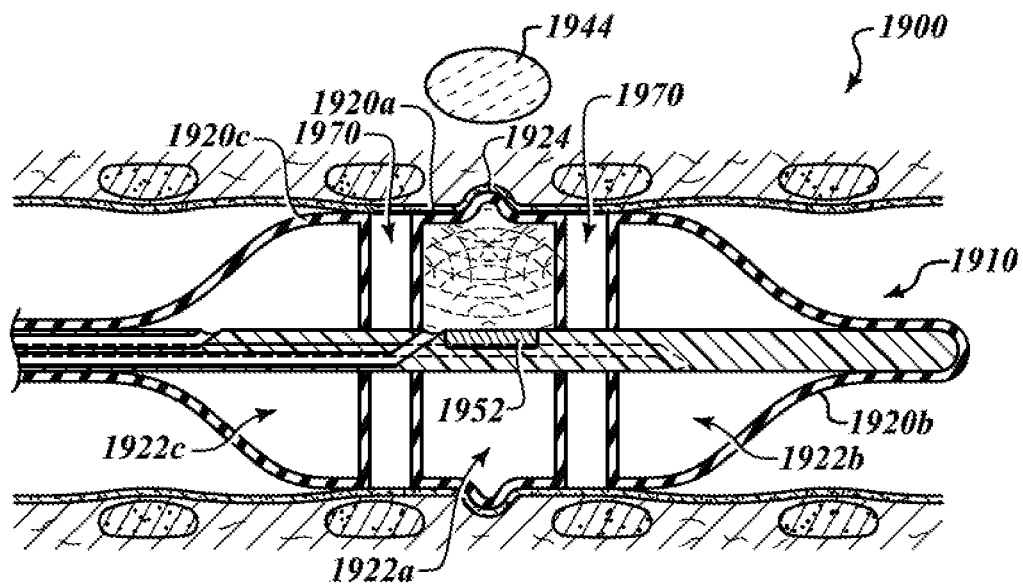
FIG. 31 is a cross-sectional view of a pulmonary treatment system according to another aspect.

FIG. 31 shows an example of a pulmonary treatment system 1900 including an ultrasound energy delivery assembly 1910 having a plurality of expandable members 1920a-c, which can be inflated independently or concurrently by introducing fluid into respective internal chambers 1922a-c thereof. The expandable members 1920a-c are arranged to provide intermediate spaces 1970 between the expandable members 1920a-c to provide acoustic barriers or shields that reduce or minimize the transmission of ultrasound energy in select areas to focus or isolate the transmission of ultrasound energy to a desired region that corresponds to an interface between the central expandable member 1920a and surface tissue 105 of the airway between a treatment zone 1944 and the ultrasound energy delivery assembly 1910. An ultrasound energy delivery element 1952 is provided within the central expandable member 1920a to selectively generate ultrasound energy for delivery to the treatment zone 1944. In some embodiments, the central expandable member 1920a may include a seating portion 1924 to seat between adjacent cartilage rings 28. The ultrasound energy delivery element 1952 may be aligned with the seating portion 1924 when provided.

The central expandable member 1920a may be of a width that is sized to contact the wall of the airway on in the intercartilaginous space between adjacent cartilage rings. The intermediate spaces 1970 may be of sufficient width to substantially prevent ultrasound energy transmission across the spaces 1970, but otherwise may be relatively thin such that the opposing expandable members 1920b, 1920c may be used to assist in effectively cooling surface tissue near the contact interface with the wall of the airway. The spaces 1970 shown in FIG. 31 are exaggerated for clarity.

Figure 32:
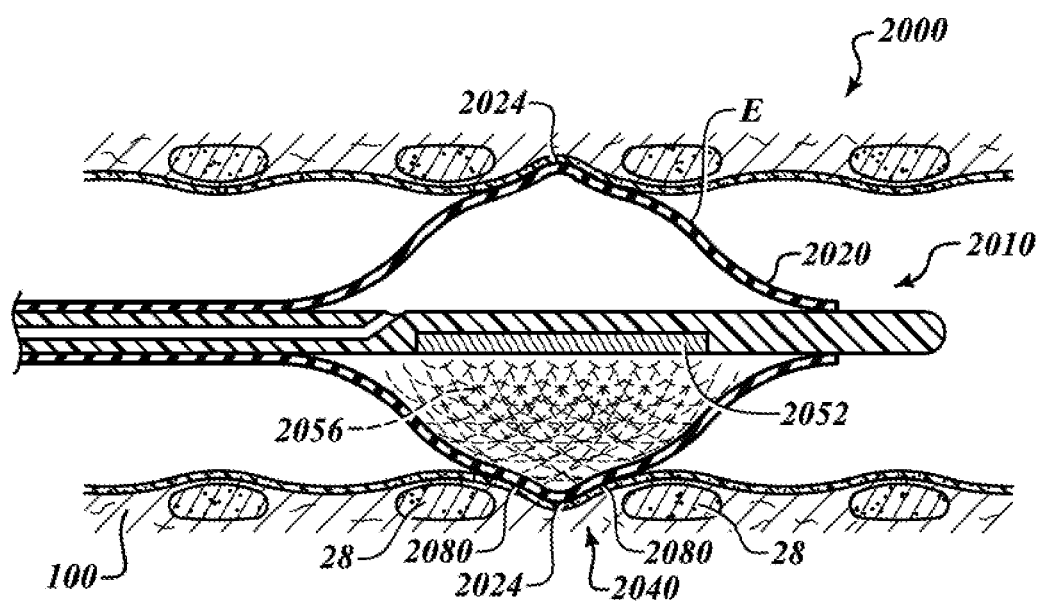
FIG. 32 is a cross-sectional view of a pulmonary treatment system according to another aspect.

FIG. 32 shows an example pulmonary treatment system 2000 including an ultrasound energy delivery assembly 2010 having an expandable member 2020 that includes a curvilinear surface profile in an expanded configuration E and that has a material, thickness, and geometry selected to reflect and focus ultrasound energy emitted by an ultrasound energy delivery element 2052 positioned therein toward an area 2040 defined by an interface of a seating portion 2024 of the expandable member 2020 and the airway wall between adjacent cartilage rings 28 of the airway 100, as illustrated by the wave fronts labeled 2056. In this manner, ultrasound energy may be redirected or focused to pass through the interface defined by the seating portion 2024 and immediately adjacent portions 2080 of the expandable member 2020 located proximally and distally of the seating portion 2024.

Figure 33:
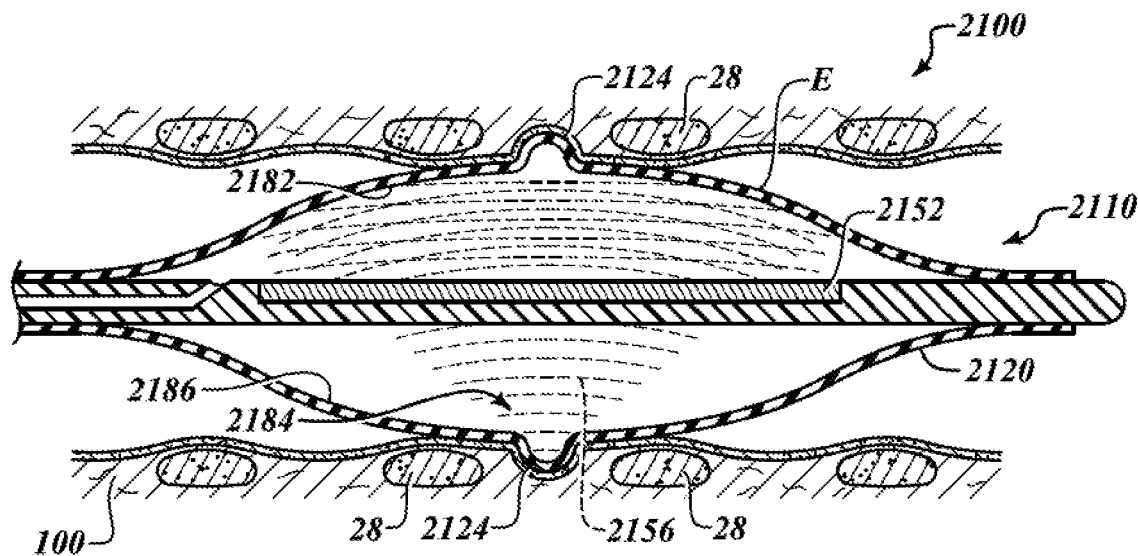
FIG. 33 is a cross-sectional view of a pulmonary treatment system according to another aspect.

FIG. 33 shows an example pulmonary treatment system 2100 including an ultrasound energy delivery assembly 2110 having an expandable member 2120 that includes a curvilinear surface profile in an expanded configuration E that is shaped to reflect and redirect a substantial portion or majority of the ultrasound energy arising from an ultrasound energy delivery element 2152 positioned therein from one side 2182 of the expandable member 2120 toward an interface region 2184 on the opposing side 2186 of the expandable member 2120, as illustrated by the wave fronts labeled 2156. In this manner, a relatively long transducer may be used, which is able to advantageously maintain a near field or Fresnel zone for a greater depth. This can be beneficial in reaching a treatment zone that is radially offset from the surface tissue with sufficient energy to cause denervation.

Figure 34:
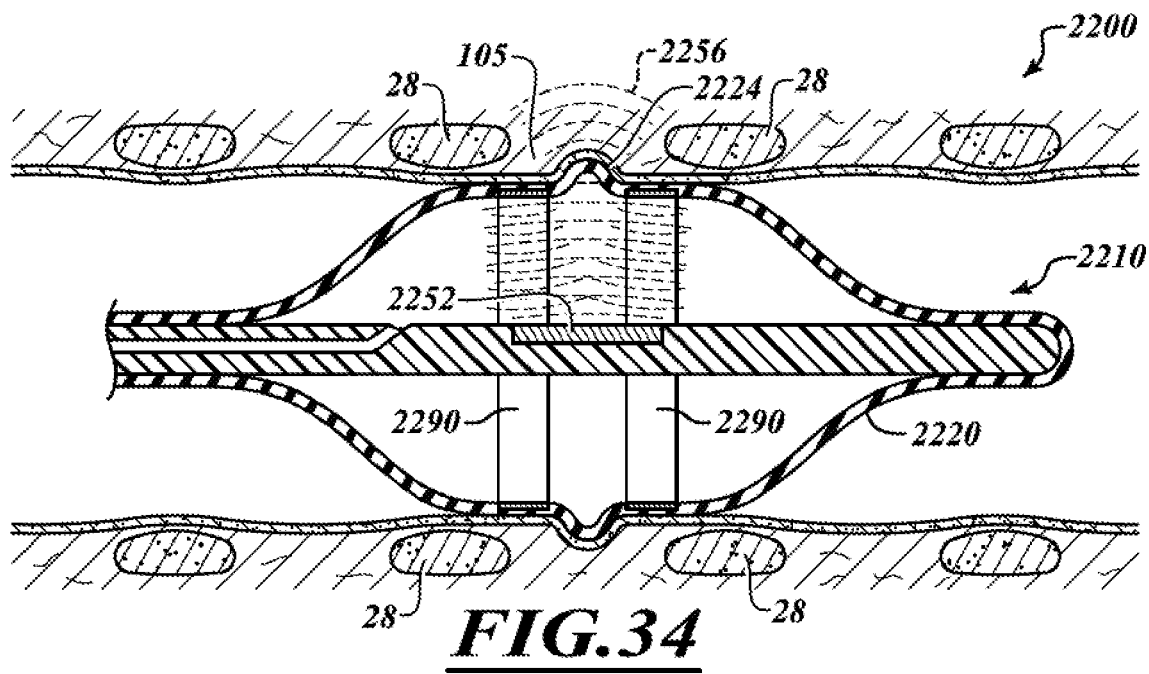
FIG. 34 is a cross-sectional view of a pulmonary treatment system according to another aspect.

FIG. 34 shows an example pulmonary treatment system 2200 including an ultrasound energy delivery assembly 2210 having an expandable member 2220 and an acoustic shield or barrier 2290 coupled to the expandable member 2220 to reduce or eliminate the transmission of ultrasound energy through surface tissue 105 of the airway wall adjacent the acoustic shield(s) or barrier(s) 2290. The acoustic shield or barrier 2290 may comprise material, such as, for example, gold foil, applied to an interior or exterior surface of the expandable member 2220. The material preferably has a high thermal conductivity to enable effective cooling of surface tissue 105 that may be adjacent thereto. The material may also have a high attenuation coefficient to absorb ultrasound energy or an impedance value selected to reflect a substantial portion of the ultrasound energy so as to reduce, minimize or substantially eliminate the amount of ultrasound energy that passes outwardly through the acoustic shield or barrier 2290. In other embodiments, acoustic shields or barriers may include inflatable sacs or other structures that are arranged to block or hinder the transmission of ultrasound energy in select directions. In this manner, ultrasound energy arising from an ultrasound energy delivery element 2252 disposed within the expandable member 2220 may be shielded from reaching tissue which is not intended to be treated, such as, for example, cartilage rings 28, or the energy may otherwise be substantially diminished before interacting with such tissue. The ultrasound energy may be focused or concentrated to pass through the expandable member 2220 only at a desired location, such as, for example, at an interface of a seating portion 2224 of the expandable member 2220 with the surface tissue 105 of the airway 100, as represented by the wave fronts labeled 2256.

The treatment systems, components and methods disclosed herein can be used as an adjunct during another medical procedure, such as minimally invasive procedures, open procedures, semi-open procedures, or other surgical procedures (e.g., lung volume reduction surgery) that provide access to a desired target site. Various surgical procedures on the chest may provide access to lung tissue or the like. Access techniques and procedures used to provide access to a target region can be performed by a surgeon and/or a robotic system. Those skilled in the art recognize that there are many different ways that a target region can be accessed.

The delivery devices disclosed herein can be used with guidewires, delivery sheaths, optical instruments, introducers, trocars, biopsy needles, or other suitable medical equipment. If the target treatment site is at a distant location in the patient (e.g., a treatment site near the lung root 24 of FIG. 1), a wide range of instruments and techniques can be used to access the site. The flexible elongated assemblies can be easily positioned within the patient using, for example, steerable delivery devices, such as endoscopes and bronchoscopes, including side-by side delivery of treatment devices with a flexible bronchoscope and delivery through the working channel of a rigid bronchoscope.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The aspects and techniques disclosed herein can be used with other procedures, such as bronchial thermoplasty.

The various embodiments and aspects described above can be combined to provide further embodiments and aspects. These and other changes can be made to the embodiments in light of the above-detailed description. The aspects, embodiments, features, systems, devices, materials, methods and techniques described herein may, in some embodiments, be similar to any one or more of the embodiments, features, systems, devices, materials, methods and techniques described in U.S. Pat. No. 8,088,127, PCT Application No. PCT/US2010/056424 filed Nov. 11, 2010 (Publication No. WO 2011/060200), U.S. application Ser. No. 12/913,702 filed on Oct. 27, 2010, U.S. application Ser. No. 12/944,666 filed Nov. 11, 2010, U.S. application Ser. No. 13/081,406 filed on Apr. 6, 2011, and U.S. Provisional Application No. 61/543,759. Further the systems disclosed herein can employ any of the cooling systems described in U.S. Provisional Patent Application Ser. No. 61/779,371, filed on Mar. 13, 2013. Each of these applications is incorporated herein by reference in its entirety. In addition, the aspects, embodiments, features, systems, devices, materials, methods and techniques described herein may, in certain embodiments, be applied to or used in connection with any one or more of the embodiments, features, systems, devices, materials, methods and techniques disclosed in the above-mentioned applications and patents.

Unless the context requires otherwise, throughout the specification and claims which follow, the word "comprise" and variations thereof, such as "comprises" and "comprising" are to be construed in an open, inclusive sense, that is, as "including but not limited to."

In general, in the following claims, the terms used should not be construed to limit the claims to the specific embodiments and aspects disclosed in the specification and the claims, but should be construed to include all possible embodiments and aspects along with the full scope of equivalents to which such claims are entitled. Accordingly, the claims are not limited by the disclosure.

What is claimed is:

1. A pulmonary treatment system, comprising:
   an elongate body; and
   an ultrasound energy delivery assembly coupled to a distal end of the elongate body and being positionable into an airway of a patient, the airway having first and second interior surfaces on opposing sides thereof, wherein the ultrasound energy delivery assembly comprises an apposition member, a fluid conduit having an elongate portion extending along an exterior surface of the apposition member, and an ultrasound energy delivery element extending along the elongate portion of the fluid conduit, the ultrasound energy delivery assembly being movable from a delivery state to a deployed state,
   wherein the apposition member is configured to urge the fluid conduit closer to and into contact with the first interior surface of the airway when the ultrasound energy delivery assembly is in the deployed state to position the ultrasound delivery element closer to a treatment site located radially outward from the first interior surface,
   wherein, in the deployed state, the elongate portion of the fluid conduit with the ultrasound energy delivery element extends longitudinally along the exterior surface of the apposition member and parallel to a longitudinal axis of the apposition member, the ultrasound delivery element being positioned outside of the fluid conduit between the fluid conduit and the apposition member such that the ultrasound delivery element is completely or substantially concealed between the fluid conduit and the apposition member, and
   wherein the ultrasound energy delivery element is configured to deliver ultrasound energy to the treatment site.

2. The pulmonary treatment system of claim 1, wherein the apposition member is configured to urge the ultrasound delivery element away from the second interior surface of the airway wall when moved from the delivery state to the deployed state.

3. The pulmonary treatment system of claim 2, wherein the apposition member comprises an expandable member for moving the ultrasound energy delivery assembly from the delivery state to the deployed state.

4. The pulmonary treatment system of claim 3, wherein the expandable member is in fluid communication with a supply lumen and a return lumen to enable an acoustic coupling fluid to circulate through the expandable member.

5. The pulmonary treatment system of claim 3, wherein the expandable member comprises an inflatable balloon.

6. The pulmonary treatment system of claim 3, wherein the expandable member comprises an expandable basket structure.

7. The pulmonary treatment system of claim 1, wherein the ultrasound energy delivery element is positioned on an exterior surface of the fluid conduit.

8. The pulmonary treatment system of claim 1, wherein the ultrasound delivery element extends parallel to a longitudinal axis of the fluid conduit.

9. The pulmonary treatment system of claim 1, wherein the fluid conduit is configured for fluid circulation therethrough to remove heat from tissue abutting the tissue contacting surface of the fluid conduit during ultrasound energy delivery to the treatment site by the ultrasound delivery element.

* * * * *